United States Patent
Royalty et al.

(10) Patent No.: US 7,842,707 B2
(45) Date of Patent: Nov. 30, 2010

(54) PEPTIDASE INHIBITORS

(75) Inventors: Susan Marie Royalty, Cary, NC (US); James Ford Burns, Glen Ridge, NJ (US); Jan Jozef Scicinski, Sunnyvale, CA (US); Gunnar Erik Jagdmann, Jr., Apex, NC (US); Robert James Foglesong, Durham, NC (US); Kellee Griffin Ring, Garner, NC (US); Tatyana Dyakonov, Durham, NC (US); David Middlemiss, Hertfordshire (GB)

(73) Assignee: Nuada, LLC, Durham, NC (US)

( * ) Notice: Subject to any disclaimer, the term of this patent is extended or adjusted under 35 U.S.C. 154(b) by 311 days.

(21) Appl. No.: 11/571,857

(22) PCT Filed: Jul. 21, 2005

(86) PCT No.: PCT/US2005/025837
§ 371 (c)(1),
(2), (4) Date: Jan. 16, 2008

(87) PCT Pub. No.: WO2006/012395
PCT Pub. Date: Feb. 2, 2006

(65) Prior Publication Data
US 2008/0234292 A1    Sep. 25, 2008

Related U.S. Application Data

(60) Provisional application No. 60/590,541, filed on Jul. 23, 2004, provisional application No. 60/634,362, filed on Dec. 8, 2004.

(51) Int. Cl.
A01N 43/40 (2006.01)
A01N 43/78 (2006.01)
A01N 43/80 (2006.01)
A01N 43/36 (2006.01)
A61K 31/44 (2006.01)
A61K 31/425 (2006.01)
A61K 31/42 (2006.01)
A61K 31/40 (2006.01)
C07D 401/00 (2006.01)
C07D 277/00 (2006.01)
C07D 261/00 (2006.01)
C07D 295/00 (2006.01)

(52) U.S. Cl. .............. 514/343; 514/365; 514/380; 514/423; 546/279.1; 548/200; 548/243; 548/540

(58) Field of Classification Search .............. None
See application file for complete search history.

(56) References Cited

U.S. PATENT DOCUMENTS

| | | | |
|---|---|---|---|
| 6,011,155 A | 1/2000 | Villhauer | 544/333 |
| 6,166,063 A | 12/2000 | Villhauer | 514/423 |
| 6,172,081 B1 | 1/2001 | Damon | 514/307 |
| 6,303,661 B1 | 10/2001 | Demuth et al. | 514/866 |
| 6,319,893 B1 | 11/2001 | Demuth et al. | 514/2 |
| 6,395,767 B2 | 5/2002 | Robl et al. | 514/412 |
| 6,432,969 B1 | 8/2002 | Villhauer | 514/275 |
| 6,500,804 B2 | 12/2002 | Demuth et al. | 514/19 |
| 6,548,481 B1 | 4/2003 | Demuth et al. | 514/19 |
| 6,559,314 B2 | 5/2003 | Demuth et al. | 548/146 |
| 6,573,287 B2 | 6/2003 | Sulsky et al. | 514/378 |
| 6,617,340 B1 | 9/2003 | Villhauer | 514/343 |
| 6,645,995 B2 | 11/2003 | Kanstrup et al. | 514/422 |
| 6,699,871 B2 | 3/2004 | Edmondson et al. | 514/249 |
| 6,706,742 B2 | 3/2004 | De Nanteuil et al. | 514/365 |
| 6,803,357 B1 | 10/2004 | Bachovchin et al. | 514/2 |
| 6,844,316 B2 | 1/2005 | Niestroj et al. | 514/19 |
| 6,890,905 B2 | 5/2005 | Demuth et al. | 514/19 |
| 6,946,480 B2 | 9/2005 | Demuth et al. | 514/365 |
| 6,949,515 B2 | 9/2005 | Demuth et al. | 514/19 |
| 7,053,055 B2 | 5/2006 | Demuth et al. | 514/18 |
| 7,060,719 B2 | 6/2006 | Demuth et al. | 514/365 |
| 7,084,120 B2 | 8/2006 | Demuth et al. | 514/19 |
| 2001/0020006 A1 | 9/2001 | Demuth et al. | 514/19 |
| 2002/0006899 A1 | 1/2002 | Pospisilik et al. | 514/2 |
| 2002/0049164 A1 | 4/2002 | Demuth et al. | 514/19 |
| 2002/0071838 A1 | 6/2002 | Demuth et al. | 424/94.61 |
| 2003/0078247 A1 | 4/2003 | De Nanteuil et al. | 514/183 |

(Continued)

FOREIGN PATENT DOCUMENTS

EP    1 338 595    8/2003

(Continued)

OTHER PUBLICATIONS

Wolff et. al., "Burger's Medicinal Chemistry and Drug Discovery," 5th Ed. Part 1, pp. 975-977 (1995).*

(Continued)

Primary Examiner—James O Wilson
Assistant Examiner—Jeffrey H Murray
(74) Attorney, Agent, or Firm—Myers Bigel Sibley & Sajovec, PA

(57) ABSTRACT

The present invention relates to a series of novel compounds having the formula (I) wherein: X is $NR^3$ or O; n is 1 or 2; A is a bicyclic carbocycle and R1 and R2 are as described herein. The compounds are useful as DPP-IV inhibitors, such as for the treatment of diabetes.

(I)

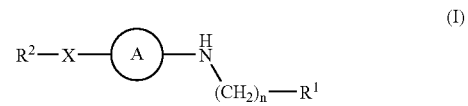

20 Claims, No Drawings

U.S. PATENT DOCUMENTS

| | | |
|---|---|---|
| 2003/0087950 A1 | 5/2003 | DeNanteuil et al. ......... 514/422 |
| 2003/0092630 A2 | 5/2003 | Demuth et al. ................ 514/14 |
| 2003/0119736 A1 | 6/2003 | Demuth et al. ................ 514/12 |
| 2003/0119738 A1 | 6/2003 | Niestroj et al. ................ 514/12 |
| 2003/0119750 A1 | 6/2003 | Demuth et al. ................ 514/19 |
| 2003/0125304 A1 | 7/2003 | Demuth et al. ................ 514/80 |
| 2003/0130199 A1 | 7/2003 | von Hoersten et al. ........ 514/17 |
| 2003/0135023 A1 | 7/2003 | Demuth et al. ............. 530/329 |
| 2003/0148961 A1 | 8/2003 | Heiser et al. .................. 514/19 |
| 2003/0162820 A1 | 8/2003 | Demuth et al. ............. 514/365 |
| 2003/0176357 A1 | 9/2003 | Pospisilik et al. ............. 514/17 |
| 2003/0199528 A1 | 10/2003 | Kanstrup et al. ......... 514/263.2 |
| 2003/0216450 A1 | 11/2003 | Evans et al. ................ 514/365 |
| 2003/0232761 A1 | 12/2003 | Hinke et al. .................. 514/14 |
| 2003/0236272 A1 | 12/2003 | Carr ........................ 514/263.2 |
| 2004/0002609 A1 | 1/2004 | Hulin ......................... 548/538 |
| 2004/0034014 A1 | 2/2004 | Kanstrup et al. ............. 514/218 |
| 2004/0058876 A1 | 3/2004 | Hoffmann et al. ............. 514/17 |
| 2004/0063935 A1 | 4/2004 | Yasada et al. .................. 544/60 |
| 2004/0106655 A1 | 6/2004 | Kitajima et al. ............. 514/365 |
| 2004/0106656 A1 | 6/2004 | Ashton et al. ............... 514/365 |
| 2004/0110817 A1 | 6/2004 | Hulin ......................... 514/408 |
| 2004/0121964 A1 | 6/2004 | Madar et al. .................. 514/19 |
| 2004/0132713 A1 | 7/2004 | Hulin et al. ............ 514/210.17 |
| 2004/0152745 A1 | 8/2004 | Jackson et al. .............. 514/365 |
| 2004/0167133 A1 | 8/2004 | Edmondson et al. ........ 514/249 |
| 2004/0167191 A1 | 8/2004 | Demuth et al. .............. 514/365 |
| 2004/0167341 A1 | 8/2004 | Haffner et al. .............. 548/200 |
| 2004/0171555 A1 | 9/2004 | Demuth et al. ................ 514/18 |
| 2004/0171848 A1 | 9/2004 | Haffner et al. .............. 548/517 |
| 2004/0176428 A1 | 9/2004 | Edmondson et al. ........ 514/365 |
| 2004/0209891 A1 | 10/2004 | Broqua .................. 514/252.05 |
| 2004/0214762 A1 | 10/2004 | Demuth et al. ................ 514/12 |

FOREIGN PATENT DOCUMENTS

| | | |
|---|---|---|
| EP | 1 354 882 | 10/2003 |
| EP | 1 280 797 | 10/2004 |
| JP | 2004002367 | 1/2004 |
| WO | 91/16339 | 10/1991 |
| WO | 93/08259 | 4/1993 |
| WO | 95/15309 | 6/1995 |
| WO | 98/18763 | 5/1998 |
| WO | 98/19998 | 5/1998 |
| WO | 99/67278 | 12/1999 |
| WO | 00/34241 | 6/2000 |
| WO | WO 0034241 A1 | 6/2000 |
| WO | 01/40180 | 6/2001 |
| WO | 01/52825 | 7/2001 |
| WO | 01/81337 | 11/2001 |
| WO | 02/14271 | 2/2002 |
| WO | 02/30890 | 4/2002 |
| WO | 02/30891 | 4/2002 |
| WO | 02/38541 | 5/2002 |
| WO | 02/051836 | 7/2002 |
| WO | 02/076450 | 10/2002 |
| WO | 02/083109 | 10/2002 |
| WO | 02/092582 | 11/2002 |
| WO | 03/000250 | 1/2003 |
| WO | 03/002530 | 1/2003 |
| WO | 03/002531 | 1/2003 |
| WO | 03/002553 | 1/2003 |
| WO | 03/002593 | 1/2003 |
| WO | 03/024942 | 3/2003 |
| WO | 03/024965 | 3/2003 |
| WO | 03/029200 | 4/2003 |
| WO | 03/033524 | 4/2003 |
| WO | 03/035057 | 5/2003 |
| WO | 03/037327 | 5/2003 |
| WO | 03/038123 | 5/2003 |
| WO | 03/040174 | 5/2003 |
| WO | 03/045977 | 6/2003 |
| WO | 03/051848 | 6/2003 |
| WO | 03/055881 | 7/2003 |
| WO | 03/057144 | 7/2003 |
| WO | 03/057666 | 7/2003 |
| WO | 03/068748 | 8/2003 |
| WO | 03/068757 | 8/2003 |
| WO | 03/069303 | 8/2003 |
| WO | 03/074500 | 9/2003 |
| WO | 03/075836 | 9/2003 |
| WO | 03/080070 | 10/2003 |
| WO | 03/080633 | 10/2003 |
| WO | 03/082817 | 10/2003 |
| WO | 03/84940 | 10/2003 |
| WO | 03/084940 | 10/2003 |
| WO | 03/095425 | 11/2003 |
| WO | 03/099279 | 12/2003 |
| WO | 03/101448 | 12/2003 |
| WO | 03/101449 | 12/2003 |
| WO | 03/106456 | 12/2003 |
| WO | 2004/007446 | 1/2004 |
| WO | 2004/007468 | 1/2004 |
| WO | 2004/009544 | 1/2004 |
| WO | 2004/014860 | 2/2004 |
| WO | 2004/016587 | 2/2004 |
| WO | 2004/037169 | 5/2004 |
| WO | 2004/037181 | 5/2004 |
| WO | 2004/041795 | 5/2004 |
| WO | 2004/043940 | 5/2004 |
| WO | 2004/046106 | 6/2004 |
| WO | 2004/048352 | 6/2004 |
| WO | 2004/050022 | 6/2004 |
| WO | 2004/058266 | 7/2004 |
| WO | 2004/064778 | 8/2004 |
| WO | 2004/067509 | 8/2004 |
| WO | 2004/069162 | 8/2004 |
| WO | 2004/071454 | 8/2004 |
| WO | 2004/080958 | 9/2004 |
| WO | 2004/083212 | 9/2004 |
| WO | 2004/085661 | 10/2004 |
| WO | 2004/087503 | 10/2004 |
| WO | 2004/087650 | 10/2004 |
| WO | WO 2005/021536 A2 | 3/2005 |
| WO | 2006/012441 | 2/2006 |

OTHER PUBLICATIONS

Banker, et. al., Modern Pharmaceuticals, (1996) p. 596.*
Dorwald F. A. Side Reactions in Organic Synthesis, 2005, Wiley: VCH, Weinheim p. IX of Preface.*
International Search Report and the Written Opinion, dated Mar. 10, 2006 for corresponding PCT application No. PCT/US2005/025837 (11 pages).
Villhauer et al. "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties", *J. Med. Chem.* 46:2774-2789 (2003).
Extended European Search Report corresponding to European Patent Application No. 05783778.3 dated Jul. 23, 2009.

* cited by examiner

PEPTIDASE INHIBITORS

Related Applications

This application is a 35 USC 371 national phase application of PCT/US2005/025837, filed Jul. 21, 2005, which claims the benefit of U.S. Provisional Application Ser. Nos. 60/590,541 filed Jul. 23, 2004 and 60/634,362 filed Dec. 8, 2004, the contents of which are hereby incorporated by reference as if recited in full herein.

FIELD OF THE INVENTION

The present invention relates to a series of novel compounds that are inhibitors of the enzyme dipeptidyl peptidase IV (DPP-IV), as well as their salts, and isomers, and pharmaceutical formulations containing the same, and to methods of use thereof, particularly for treating diabetes.

BACKGROUND OF THE INVENTION

The gut incretin hormones, glucagon-like peptide-1 (GLP-1) and gastric inhibitory polypeptide (GIP) are responsible for >50% of nutrient stimulated insulin release and have roles in β-cell glucose competence, stimulating β-cell growth, differentiation, proliferation and cell survival. On release, these hormones are rapidly inactivated (GLP-1; $t_{1/2}$=1.5 min) by a ubiquitous serine protease, dipeptidyl peptidase IV (DPP-IV) which acts by specifically cleaving Pro or Ala terminal amino acid residues. Inhibition of DPP-IV has been shown to extend the half-life of GLP-1 with favorable effects on stimulation of insulin secretion, inhibition of glucagon release and slowing gastric emptying.

DPP-IV inhibition, through the preservation of active GLP-1 levels, has the potential to slow or even prevent the progression of type 2 diabetes by stimulating insulin gene expression and biosynthesis, increasing the expression of the β-cell's glucose-sensing mechanism and promoting genes involved in the differentiation of β-cells. As the glucose lowering effects of GLP-1 are dependent on elevated blood glucose and subside as glucose levels return to normal, the probability of hypoglycemia during treatment with a DPP-IV inhibitor is expected to be very low. Indeed; studies on the long term inhibition of DPP-IV and with DPP-IV knock-out mice have shown no adverse effects.

Application of DPP-IV inhibitors delays the inactivation of GIP and GLP-1 thereby allowing increased insulin secretion and improved blood glucose control. It could be shown in animal models and diabetic patients that the overall blood sugar control of the body is improved due to a restoration of proper insulin secretion and action. Such a mode of action is unique to this therapeutic principle. The above studies suggest the possibility of long term safe treatment of type-2 diabetes with DPP-IV inhibitors.

SUMMARY OF THE INVENTION

A first aspect of the present invention is a compound of Formula I:

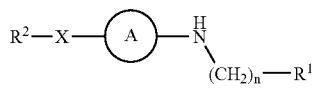

wherein:
X is $NR^3$ (wherein $R^3$ is described below) or O
n is 1 or 2;
A is a bicyclic or tricyclic carbocycle of 5 to 20 atoms wherein each bridge of the bicycle has at least one atom;
$R^1$ is

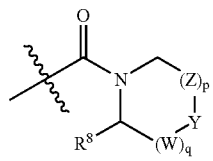

wherein:
p and q are independently 0 or 1;
Y is $CH_2$, CHF, $CF_2$, O, or S(O)m;
W and Z are independently $CH_2$, CHF, or $CF_2$;
and wherein the ring formed by N, W, Y, Z and the carbon atoms to which they are attached is saturated or optionally contains one double bond,
$R^2$ is an organic group as described further below;
$R^8$ is H or cyano;
m is 0, 1 or 2;
or a pharmaceutically acceptable salt or prodrug thereof.

A second aspect of the present invention is a pharmaceutical composition comprising a compound as described herein in combination with a pharmaceutically acceptable carrier.

A third aspect of the present invention is a method of inhibiting DPP-IV in a subject in need thereof, comprising administering said subject a compound as described herein in an amount effective to inhibit DPP-IV in said subject.

A fourth aspect of the present invention is a method of treating diabetes (particularly type II diabetes) in a subject in need thereof, comprising administering said subject a compound as described herein in an amount effective to treat said diabetes.

A fifth aspect of the present invention is the use of a compound or active compound as described herein for the preparation of a medicament useful for a method of use or treatment as described herein.

In some embodiments, the administering step is a transdermal administering step (e.g., an active transdermal administering step, such as an iontophoresis, electroporation, sonophoresis, thermal energy, or magnetophoresis, or is carried out by applying a patch containing said active agent to the skin of said subject).

In some embodiments, the administering step is carried out by inhalation administration (e.g., by intranasal spray, and/or by inhalation to the lungs of said subject)

A further aspect of the invention is, in a transdermal drug delivery device, the improvement comprising employing an active compound as described herein as the active agent in the device. Such devices include a patch (e.g., a patch comprising a backing and at least one adhesive layer carried by said backing, with said adhesive layer further comprising said active agent; a patch comprising a backing, a reservoir connected to said backing, and an adhesive layer, with said reservoir further comprising said active agent; a patch comprising a backing, a matrix connected to said backing, and an adhesive layer, with said matrix further comprising said active agent) and in some embodiments optionally further comprise a plurality of microneedles operatively associated therewith and configured for increasing flux of said active agent across the skin of a subject.

A further aspect of the invention is, in an inhalation drug delivery device, the improvement comprising employing an active agent as described herein as the active agent in the device. Suitable devices include a nasal spray devices and lung administration devices.

The foregoing and other objects and aspects of the present invention are explained in greater detail in the specification set forth below.

DETAILED DESCRIPTION OF THE PREFERRED EMBODIMENTS

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Hydroxyl" as used herein refers to an —OH group.

"Nitro" as used herein refers to an —$NO_2$ group.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of Alkenyl include, but are not limited to, vinyl, 2-propenyl, 3-butenyl, 2-butenyl, 4-pentyl, 3-pentyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of Alkynyl include, but are not limited to, 2-propynyl, 3-butynyl, 2-butynyl, 4-pentenyl, 3-pentenyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Alkoxy," as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl," as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio," as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl," as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl," as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl; alkenyl, alkynyl, cycloalkyl, cycloalkylalkyl, aryl, arylalkyl, heterocyclo, heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl," as used herein alone or as part of another group, refers to a saturated or partially unsaturated cyclic hydrocarbon group containing from 3, 4 or 5 to 6, 7 or 8 carbons (which may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with halo or loweralkyl.

"Heterocyclic group" or "heterocyclo" as used herein alone or as part of another group, refers to a monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Treat" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

Prodrugs of the present invention include esters or compositions as described in U.S. Pat. No. 6,548,668 to Adams et al., U.S. Pat. No. 6,083,903 to Adams et al., or U.S. Pat. No. 6,699,835 to Plamondon et al., the disclosures of which are incorporated by reference herein in their entirety.

1. Active Compounds.

Active compounds of the present invention (this term including pharmaceutically acceptable salts and prodrugs thereof) can be made in accordance with known techniques (see, e.g., U.S. Pat. No. 6,166,063 to Villhauer et al.) or variations thereof which will be apparent to those skilled in the art based on the disclosure provided herein.

Thus compounds or active compounds of the present invention are illustrated by Formula I:

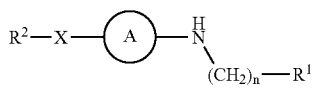

wherein:

X is NR³ or O;

n is 1 or 2;

A is a bicyclic or tricyclic carbocycle of 5 to 20 atoms wherein each bridge of the bicycle has at least one atom;

R¹ is

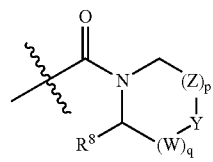

wherein:

p and q are independently 0 or 1;

Y is CH₂, CHF, CF₂, O, or S(O)m;

W and Z are independently CH₂, CHF, or CF₂;

and wherein the ring formed by N, W, Y, Z and the carbon atoms to which they are attached is saturated or optionally contains one double bond;

When X=NR³ then R² is R⁴—SO₂—; R⁵—SO₂—NH—C(O)—; R⁶R⁷N—SO₂—; or a heterocyclic group unsubstituted or optionally substituted with halo, alkyl, haloalkyl, alkenyl, alkynyl, cycloalkyl, cycloalkylalkyl, aryl, arylalkyl, heterocyclo, heterocycloalkyl, hydroxyl, alkoxy, haloalkyloxy, cycloalkyloxy, cycloalkylalkyloxy, aryloxy, arylalkyloxy, heterocyclooxy, heterocycloalkyloxy, mercapto, alkyl-S(O)ₘ, haloalkyl-S(O)ₘ, cycloalkyl-S(O)ₘ, cycloalkylalkyl-S(O)ₘ, aryl-S(O)ₘ, arylalkyl-S(O)ₘ, heterocyclo-S(O)ₘ, heterocycloalkyl-S(O)ₘ, amino, alkylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano;

When X=O then R² is a heterocyclic group unsubstituted or optionally substituted with halo, alkyl, haloalkyl, alkenyl, alkynyl, cycloalkyl, cycloalkylalkyl, aryl, arylalkyl, heterocyclo, heterocycloalkyl, hydroxyl, alkoxy, haloalkyloxy, cycloalkyloxy, cycloalkylalkyloxy, aryloxy, arylalkyloxy, heterocyclooxy, heterocycloalkyloxy, mercapto, alkyl-S(O)ₘ, haloalkyl-S(O)ₘ, cycloalkyl-S(O)ₘ, cycloalkylalkyl-S(O)ₘ, aryl-S(O)ₘ, arylalkyl-S(O)ₘ, heterocyclo-S(O)ₘ, heterocycloalkyl-S(O)ₘ, amino, alkylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano;

R³ is selected from the group consisting of H, alkyl, haloalkyl, alkenyl, alkynyl, cycloalkyl, cycloalkylalkyl, aryl, arylalkyl, heterocyclo, and heterocycloalkyl;

R⁴ is selected from the group consisting of: haloalkyl, alkenyl, alkynyl, cycloalkyl, cycloalkylalkyl, aryl, arylalkyl, heterocyclo, and heterocycloalkyl; preferably aryl, heterocyclo, and heterocycloalkyl;

R⁵ is selected from the group consisting of alkyl, haloalkyl, alkenyl, alkynyl, cycloalkyl, cycloalkylalkyl, aryl, arylalkyl, heterocyclo, and heterocycloalkyl;

R⁶ and R⁷ are each independently selected from the group consisting of: H, alkyl, haloalkyl, alkenyl, alkynyl, cycloalkyl, cycloalkylalkyl, aryl, arylalkyl, heterocyclo, and heterocycloalkyl; or R⁶ and R⁷ together form C3-C7 alkylene;

R⁸ is H or cyano;

m is 0, 1 or 2;

or a pharmaceutically acceptable salt or prodrug thereof.

Examples of suitable groups "A" include but are not limited to adamantyl, bicyclo[2.1.1]hexane, bicyclo[3.1.1]heptane, bicyclo[3.2.1]octane, bicyclo[2.2.2]octane, and bicycl[3.3.1]nonane, which may be optionally include one or more double bonds.

Examples of suitable adamantyl groups "A" for carrying out the present invention, with linkages, include the following:

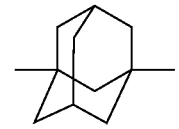

Particular examples of suitable groups "A" for carrying out the present invention, with linkages, include the following:

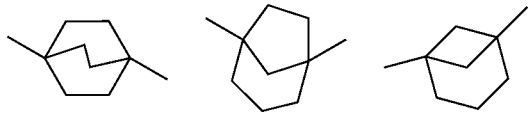

(a bicyclo[2.2.2]octane)(a bicyclo[3.2.1]octane)(a bicyclo[3.1.1]heptane)

Examples of active compounds of the present invention include but are not limited to:

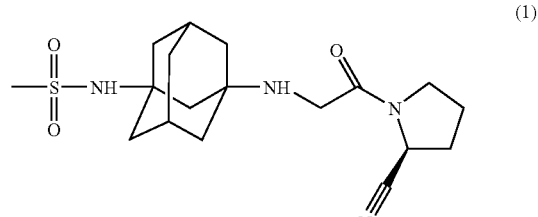

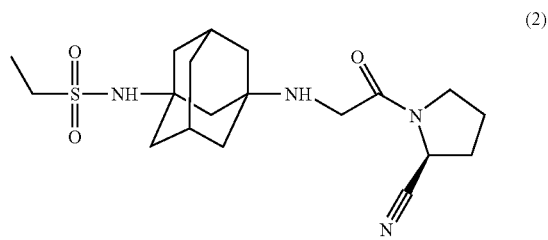

-continued

Additional examples of compounds of the invention include, but are not limited to:

-continued

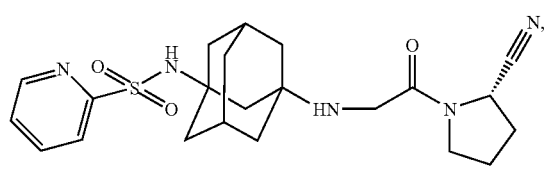
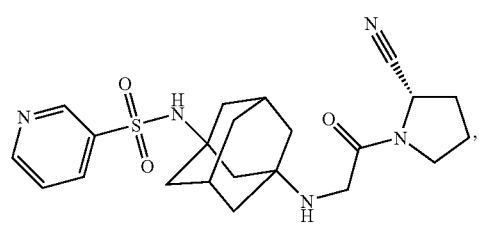
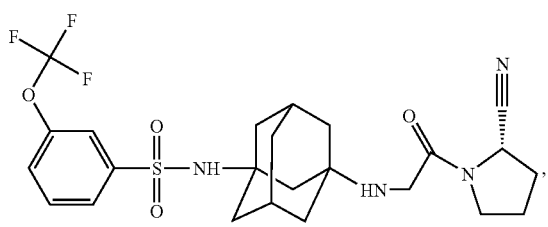
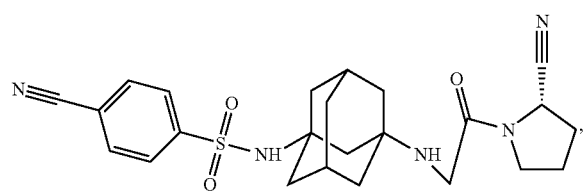
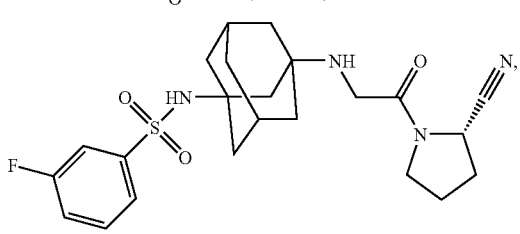
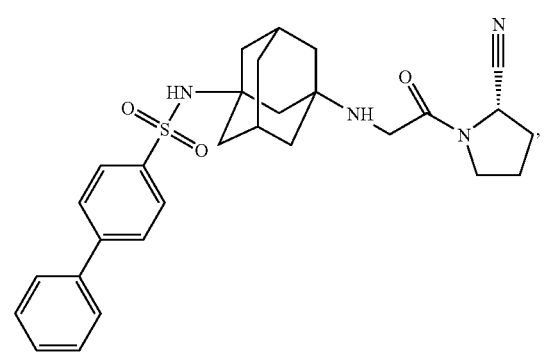
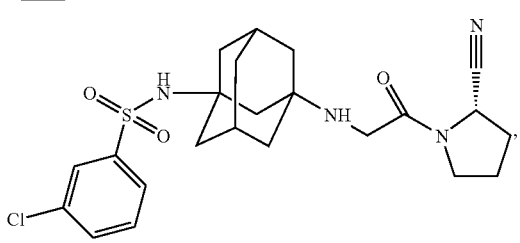

-continued

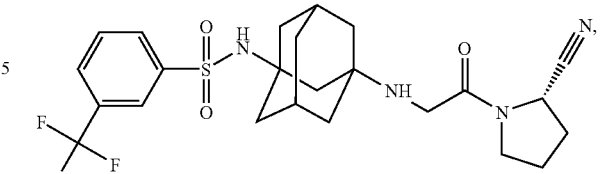
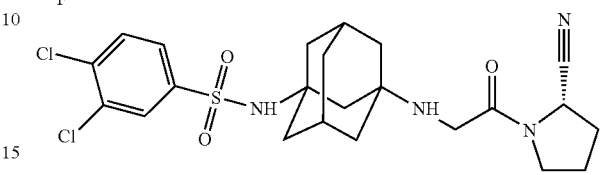
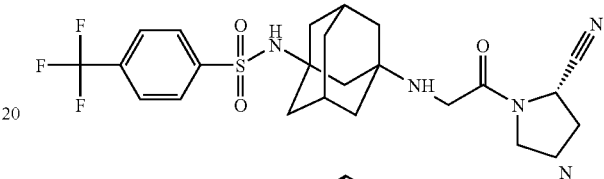
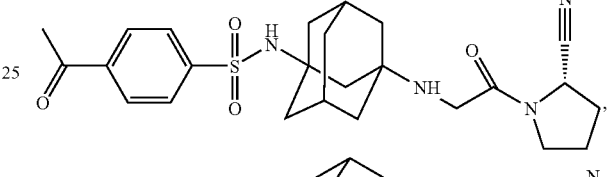
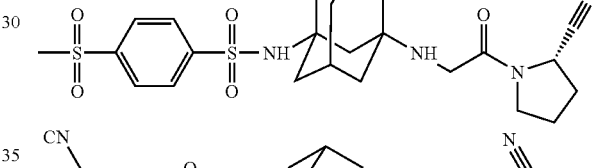
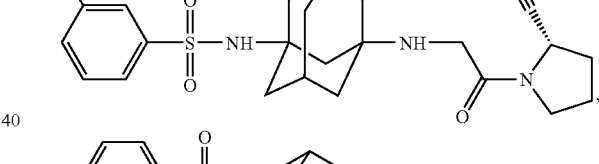
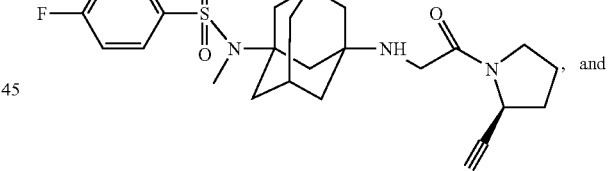
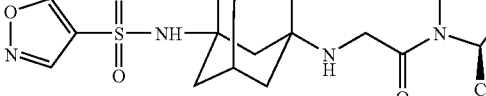

Certain of the compounds described herein contain one or more chiral centers, or may otherwise be capable of existing as multiple stereoisomers. The scope of the present invention includes pure stereoisomers as well as mixtures of stereoisomers, such as purified enantiomers/diastereomers, enantiomerically/diastereomerically enriched mixtures or racemates.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/ dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques. Liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to the active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Subjects.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. The subjects may be male or female and may be of any suitable age, including infant, juvenile, adolescent, and adult subjects.

Subjects to be treated with active compounds, or administered active compounds, of the present invention are, in general, subjects in which dipeptidyl peptidase IV (DPP-IV) is to be inhibited.

Subjects in need of such treatment include, but are not limited to, subjects afflicted with diabetes, especially Type II diabetes, as well as impaired glucose homeostasis, impaired glucose tolerance, infertility, polycystic ovary syndrome, growth disorders, frailty, arthritis, allograft rejection in transplantation, autoimmune diseases, AIDS, intestinal diseases, inflammatory bowel syndrome, anorexia nervosa, osteoporosis, hyperglycemia, Syndrome X, diabetic complications, hyperinsulinemia, obesity, atherosclerosis and related diseases, as well as various immunomodulatory diseases and chronic inflammatory bowel disease (such as Crohn's disease and ulcerative colitis), glucosuria, metabolic acidosis, cataracts, Type 1 diabetes, hypertension, hyperlipidemia, osteopenia, bone loss, bone fracture, acute coronary syndrome, short bowel syndrome, anxiety, depression, insomnia, chronic fatigue, epilepsy, chronic pain, alcohol addiction, ulcers, irritable bowel syndrome. Subjects afflicted with such diseases are administered the active compound of the present invention (including salts thereof), alone or in combination with other compounds used to treat the said disease, in an amount effective to combat or treat the disease.

A particularly preferred category of diseases for treatment by the methods of the present invention is Type II diabetes.

4. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. In general, a dosage from about 0.05 or 0.1 to about 20 or 50 mg/kg subject body weight may be utilized to carry out the present invention. For example, a dosage from about 0.1 mg/kg to about 50 mg/kg may be employed for oral administration; or a dosage of about 0.05 mg/kg to 20 mg/kg may be employed for intramuscular injection. The duration of the treatment may be one or two dosages per day for a period of two to three weeks, or until the condition is controlled or treated. In some embodiments lower doses given less frequently can be used prophylactically to prevent or reduce the incidence of recurrence of the condition being treated.

Transdermal delivery. Numerous different systems for the transdermal delivery of active agents are known. Transdermal delivery systems include but are not limited to passive devices such as drug-in-adhesive transdermal patches and "active" transdermal technologies such as iontophoresis, electroporation, sonophoresis, magnetophoresis, microneedle devices and those devices that use thermal energy to make the skin more permeable.

Transdermal drug delivery devices are available from the 3M Drug Delivery Systems Division (St. Paul, Minn., USA), Noven Pharmaceuticals, Inc. (Miami, Fla., USA), ImaRx (Tucson, Ariz., USA), Elan Corporation (Dublin, Ireland), Novosis AG (Miesbach, Germany), Ultrasonic Technologies (St. Albans, Vt., USA), Antares Pharma (Exton, Pa., USA), Altea Therapeutics (Tucker, Ga., USA), Iomed, Inc. (Salt Lake City, Utah, USA), MacroChem Corp (Lexington, Mass., USA), Sontra Medical Corporation (Franklin, Mass., USA), Vyteris, Inc. (Fair Lawn, N.J., USA), BioChemics, Inc. (Danvers, Mass., USA), A.P Pharma (Redwood, City, Calif., USA), MIKA Pharma GmbH (Limburgerhof, Germany), NexMed, Inc. (Robbinsville, N.J., USA), Encapsulation Systems, Inc. (Springfield, Pa., USA), Acrux Ltd (Elgin, Ill., USA), Jenapharm GmbH (Berlin, Germany), Norwood Abbey (Victoria, Australia), Novavax (Columbia, Md., USA), Genetronics Biomedical Corporation (San Diego, Calif., USA), Adherex Technologies (Research Triangle Park, N.C., USA), and AlphaRx (Ontario, Canada).

Transdermal drug delivery using patch technology is typically accomplished by using a covering element in the form of a transdermal patch device that is attached to the host at the desired drug delivery site. A typical transdermal patch structure includes a drug-in-adhesive layer sandwiched between an impermeable backing and a release liner. At the time of use, the release liner is easily removed so that the patch can be attached to the host, adhesive side down. The impermeable backing thus traps the drug-in-adhesive layer between the backing and the attachment site of the host. Over time, the drug penetrates into the host, or is topically active, in accordance with the desired therapeutic treatment. Optionally, the drug-in-adhesive formulation may include one or more compounds known as penetration enhancers that increase the delivery of the drug to the subject. (See U.S. Pat. No. 6,627,216).

Some examples of transdermal patch technology include but are not limited to those described in U.S. Pat. Nos. 6,592,893; 6,267,983 to Fuji et al.; U.S. Pat. No. 6,238,693 to Luther et al.; U.S. Pat. No. 6,211,425 to Takayasu et al.; U.S. Pat. No. 6,159,497 to LaPrade et al.; U.S. Pat. No. 6,153,216 to Cordes et al.; U.S. Pat. No. 5,948,433 to Burton et al.; U.S. Pat. No. 5,508,035 to Wang et al.; U.S. Pat. No. 5,284,660 to Lee et al.; U.S. Pat. No. 4,942,037 to Bondi et al.; and U.S. Pat. No. 4,906,463 to Cleary et al.

Iontophoresis, an active transdermal technology, uses low voltage electrical current to drive charged drugs through the skin. Those molecules with a positive charge are driven into the skin at the anode and those with a negative charge are driven into the skin at the cathode. See U.S. Pat. No. 6,622,037 to Kasamo. Additional examples of iontophoretic delivery devices for the transdermal delivery of active agents include but are not limited to those described in U.S. Pat. No. 6,564,903 to Ostrow et al.; U.S. Pat. No. 5,387,189 to Gory et al; U.S. Pat. No. 5,358,483 to Sibalis; U.S. Pat. No. 5,356,632 to Gross et al; U.S. Pat. No. 5,312,325 to Sibalis; U.S. Pat. No. 5,279,544 to Gross et al; U.S. Pat. No. 5,167,479 to Sibalis; U.S. Pat. No. 5,156,591 to Gross et al, U.S. Pat. No. 5,135,479 to Siballs et al; U.S. Pat. No. 5,088,977 to Sibalis; U.S. Pat. No. 5,057,072 to Phipps; U.S. Pat. No. 5,053,001 to Reller et al; and U.S. Pat. No. 4,942,883 to Newman.

Electroporation is similar to iontophoresis in that it uses electrical fields to aid in transport of molecules across the stratum corneum. However, rather than driving the molecules through the skin, electroporation uses high-voltage electric field pulses to create transient pores which permeabilize the stratum corneum (SC)(Prausnitz et al., Proc. Natl. Acad. Sci. 90:10504-10508 (1993); Murthy et al. J. Control. Release 98:307-315 (2004); U.S. Pat. No. 5,947,921)). Examples of electroporation technology for transdermal delivery include but are not limited to U.S. Pat. No. 6,692,456 to Eppstein et al.; U.S. Pat. No. 6,564,093 to Ostrow et al.; U.S. Pat. No. 6,517,864 to Orup Jacobsen et al.; U.S. Pat. No. 6,512,950 to Li et al.; U.S. Pat. No. 5,968,006 to Hofmann; and U.S. Pat. No. 5,749,847 to Zewart et al.

The technique of sonophoresis utilizes ultrasound to disrupting the stratum corneum, creating cavitations which disorder the lipid bilayers resulting increased drug transport. Although a variety of ultrasound conditions have been used for sonophoresis, the most commonly used conditions correspond to frequencies in the range of between one MHz and three MHz, and intensity in the range of between above zero and two $W/cm^2$ (U.S. Pat. No. 4,767,402 to Kost, et al.). Other devices use low frequency ultrasound that is less than one MHz (U.S. Pat. No. 6,234,990). Other examples of sonophoretic devices include but are not limited to those described in U.S. Pat. No. 6,491,657 to Rowe et al.; U.S. Pat. No. 6,487,447 to Weimann et al.; U.S. Pat. No. 6,190,315 to Kost et al.; U.S. Pat. No. 6,041,253 to Kost et al.; U.S. Pat. No. 5,947,921 to Johnson et al.; U.S. Pat. No. 5,906,580 to Kline-Schoder et al.; and U.S. Pat. No. 5,445,611 to Eppstein et al.

An additional method used to facilitate the transport of compounds across the stratum corneum is the use of thermal energy. Examples of the use of thermal energy technology to facilitate transport of compounds across the stratum corneum include but are not limited to those described in U.S. Pat. No. 6,780,426 to Zhang et al.; U.S. Pat. No. 6,613,350 to Zhang et al.; U.S. Pat. No. 6,465,006 to Zhang et al.; U.S. Pat. No. 6,284,266 to Zhang et al.; U.S. Pat. No. 6,261,595 to Stanley et al.; U.S. Pat. No. 6,048,337 to Svedman; U.S. Pat. No. 4,898,592 to Latzke et al.; U.S. Pat. No. 4,685,911 to Konno et al.; and U.S. Pat. No. 4,230,105 to Harwood.

Magnetophoresis, the use of magnetic energy, is an additional method used to increase drug transport across the stratum corneum. Some examples of magnetophoretic delivery devices include but are not limited to those disclosed in U.S. Pat. No. 6,564,093 to Ostrow et al.; U.S. Pat. No. 5,983,134 to Ostrow; U.S. Pat. No. 5,947,921 to Johnson et al.; U.S. Pat. No. 4,702,732 to Powers et al.

Microneedles or microstructured arrays are used to create micropores in the stratum corneum to aid in the flux of drugs across the skin. Examples of microneedle technology includes but is not limited to the disclosure in U.S. Pat. No. 6,331,310 to Roser et al. and H. Sebastien, et al, J. Pharm. Sci. 87:922-925 (1998).

Inhalation delivery. Devices for inhalation delivery of active agents, whether to the lungs or to nasal passages, are known and described in, for example, 6,080,762 to Allen et al. For example, dry powder formulations will typically comprise active agent in a dry, usually lyophilized, form of an appropriate particle size or within an appropriate particle size range. Minimum particle size appropriate for deposition within the lung is typically 0.5 μm mass median equivalent aerodynamic diameter (MMEAD), but is preferably 1 μm MMEAD, and is most preferably 2 μm MMEAD. Maximum particle size appropriate for deposition within the lung is typically 10 μm MMEAD, but is preferably 8 μm MMEAD, and is most preferably 4 μm MMEAD. A particle size of about 3 μm MMEAD is most preferred. Minimum particle size appropriate for deposition within the nose is typically 0.5 μm MMEAD, but is preferably 3 μm MMEAD, and is most preferably 5 μm MMEAD. Maximum particle size appropriate for deposition within the nose is typically 100 μm MMEAD, but is preferably 50 μm MMEAD, and is most preferably 20 μm MMEAD. Respirable powders of the active agent within the preferred size range can be produced by a variety of conventional techniques, such as jet milling, spray drying, solvent precipitation, supercritical fluid condensation, and the like. Because particle size is less important for nasal delivery, crystallization from solution may be sufficient. If it is not sufficient, it could be augmented by jet milling or ball milling.

These dry powders of appropriate MMEAD can be administered to a patient via a conventional dry powder inhalers (DPI's) which rely on the patient's breath, upon inhalation, to disperse the power into an aerosolized amount. Alternatively, the dry powder may be administered via air assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the active agent is lower than this amount, as discussed below, the active agent powder will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

When the dry powder is prepared by solvent precipitation, buffers and salts are typically used to stabilize the active agent in solution prior to particle formation. Suitable buffers include, but are not limited to, ascorbate, phosphate, citrate, acetate, and tris-HCl, typically at concentrations from about 5 mM to 50 mM. Suitable salts include sodium chloride, sodium carbonate, calcium chloride, and the like.

Liquid formulations of active agent for use in a nebulizer system, e.g., compressed air-, jet-, ultrasonic-, and piezoelectric nebulizers, can employ active agent dissolved or suspended in a pharmaceutical solvent, e.g., water, ethanol, or a mixture thereof. Typically, the minimum concentration of active agent dissolved/suspended is about 1 mg/mL, but is preferably 5 mg/mL, and is most preferably 10 mg/mL. Generally, the maximum concentration of active agent dissolved/suspended is about 100 mg/mL, but is preferably 60 mg/mL, and is most preferably 20 mg/mL. The total volume of nebulized liquid needed to deliver the aerosolized amount is generally in the range from about 0.1 mL to 5 mL.

The pharmaceutical solvent employed can also be a slightly acidic aqueous buffer (pH 4-6). Suitable buffers are as described above. Other components may be added to enhance or maintain chemical stability, including preservatives, surfactants, dispersants, or gases. Suitable preservatives include, but are not limited to, phenol, methyl paraben, paraben, m-cresol, thiomersal, benzylalkonimum chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaimetetraacetic acid, and the like. Suitable gases include, but are not limited to, nitrogen, helium, carbon dioxide, air, and the like.

Sprayer systems for respiratory and/or nasal delivery of active agent employ formulations similar to that described for nebulizers. For a description of such lung systems and others described herein, see e.g., Wolff, R. K. and Niven, R. W., "Generation of Aerosolized Drugs," J. Aerosol Med., 7:89, 1994. Nasal delivery systems have been described in Transdermal Systemic Medication, Y. W. Chien Ed., Elsevier Publishers, New York, 1985 and in U.S. Pat. No. 4,778,810, the teachings of which are herein incorporated by reference.

For use in MDI's, active agent may be dissolved or suspended in a suitable aerosol propellant, such as a chlorofluorocarbon (CFC) or a hydrofluorocarbon (HFC). Such suspensions will contain between 10 mg to 100 mg of active agent per aerosol dose. Suitable CFC's include trichloromonofluoromethane (propellant 11), dichlorotetrafluoromethane (propellant 114), and dichlorodifluoromethane (propellant 12). Suitable HFC's include tetrafluoroethane (HFC-134a) and heptafluoropropane (HFC-227).

For incorporation into the aerosol propellant, active agent is preferably processed into particles of the sizes described above for the dry powder formulations. The particles may then be suspended in the propellant as is, but are typically coated with a surfactant to enhance/facilitate their dispersion. Suitable surfactants are as defined above for liquid formulation. A propellant formulation may further include a lower alcohol, such as ethanol (up to 30% by weight) and other additives to maintain or enhance chemical stability and physiological acceptability. Additives suitable for propellant formulations include a surfactant as described above, such as sorbitals, oleic acid, and lecithins. For further information on such additives, see G. W. Hallworth. "The formulation and evaluation of pressurised metered-dose inhalers," Drug Delivery to the Lung, D. Ganderton and T. Jones (eds), Ellis Horword, Chichester, U.K., pg's 87-118.

The precise dosage of active agent necessary will vary with the age, size, sex and condition of the subject, the nature and severity of the disorder to be treated, and the like; thus, a precise effective amount should be determined by the caregiver. However, the total aerosolized dosage of active agent for the treatment of the disorder will typically be in the range from about 1 or 2 mg to 20, 50 or 100 mg/per day. Typically, the total dosage of active agent will be delivered in a few separate aerosolized doses.

The present invention is explained in greater detail in the following non-limiting Examples.

EXAMPLE 1

(S)-1-[(3-methanesulfonamido-1-adamantyl)amino]acetyl-2-cyano-pyrrolidine

A solution of (S)-1-[(3-amino-1-adamantyl)amino]acetyl-2-cyano-pyrrolidine (280 mg, 0.93 mmol) in 4 mL of acetonitrile with triethylamine (210 μL, 1.5 mmol) was made and cooled to 0° C. in the freezer. The methane sulfonyl chloride was prepared in advance as a 1 M solution in dry THF. The methane sulfonyl chloride solution (1.5 mL, 1.5 mmol) was added drop wise to the stirring cooled amine solution and the reaction allowed to warm to room temperature overnight. The crude reaction mixture was analyzed by LC/MS and showed complete conversion to product. The crude reaction mixture was evaporated to dryness and diluted to 3 mL in 3/1 acetonitrile: water. The sample was purified by reverse phase HPLC with mass directed fractionation using an acetonitrile/water gradient with TFA as a modifier. After lyophilization, 260 mg of the mono-TFA salt was isolated. 71% yield. $^1$H NMR (CD$_3$N, 400 MHz) δ 5.36 (bs, 1H), 4.72 (t, 1H, J=5.3 Hz), 3.93 (s, 2H), 3.65 (m, 1H), 3.47 (m, 1H), 3.0 (s, 3H), 2.1 to 2.4 (m, 9H), 1.9 (m, 7H), 1.63 (m, 1H).

EXAMPLE 2

(S)-1-[(3-ethanesulfonamido-1-adamantyl)amino]acetyl-2-cyano-pyrrolidine

A solution of (S)-1-[(3-amino-1-adamantyl)amino]acetyl-2-cyano-pyrrolidine (60 mg, 0.2 mmol) in 1 mL of acetonitrile with triethylamine (56 μL, 0.4 mmol) was made and cooled to 0° C. in the freezer. The 2,2,2-trifluoroethane sulfonyl chloride was prepared in advance as a 0.3 M solution in dry THF. The sulfonyl chloride solution (1.0 mL, 0.3 mmol) was added drop wise to the stirring cooled amine solution and the reaction allowed to warm to room temperature overnight. The crude reaction mixture was analyzed by LC/MS and showed complete conversion to product. The crude reaction mixture was evaporated to dryness and diluted to 3 mL in 3/1 acetonitrile: water. The sample was purified by reverse phase HPLC with mass directed fractionation using an acetonitrile/ water gradient with TFA as a modifier. After lyophilization, 15 mg of the mono-TFA salt was isolated. 15% yield. $^1$H NMR (CD$_3$N, 400 MHz) δ 5.25 (bs, 1H), 4.71 (t, 1H, J=5.5 Hz), 3.91 (s, 2H), 3.65 (dt, 1H, J=5.8, 9.7 Hz), 3.48 (dt, 1H, J=9.66, 6.6 Hz), 3.042 (q, 2H, J=7.3 Hz), 2.1 to 2.4 (m, 11H), 1.9 (m, 5H), 1.64 (m, 2H), 1.3 (t, 3H, J=7.3 Hz)

EXAMPLE 3

(S)-1-[(3-(2,2,2-trifluoro)-ethanesulfonamido-1-adamantyl)amino]acetyl-2-cyano-pyrrolidine

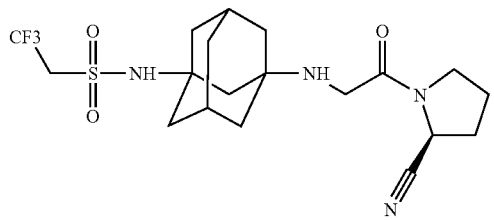

A solution of (S)-1-[(3-amino-1-adamantyl)amino]acetyl-2-cyano-pyrrolidine (60 mg, 0.2 mmol) in 1 mL of acetonitrile with triethylamine (56 μl, 0.4 mmol) was made and cooled to 0° C. in the freezer. The ethane sulfonyl chloride was prepared in advance as a 0.3 M solution in dry THF. The ethane sulfonyl chloride solution (1.0 mL, 0.3 mmol) was added drop wise to the stirring cooled amine solution and the reaction allowed to warm to room temperature overnight. The crude reaction mixture was analyzed by LC/MS and showed complete conversion to product. The crude reaction mixture was evaporated to dryness and diluted to 3 mL in 3/1 acetonitrile: water. The sample was purified by reverse phase HPLC with mass directed fractionation using an acetonitrile/ water gradient with TFA as a modifier. After lyophilization, 10 mg of the mono-TFA salt was isolated. 10% yield. $^1$H NMR (CD$_3$N, 400 MHz) δ 5.96 (bs, 1H), 4.72 (t, 1H, J=5.7 Hz), 4.05 (q, 2H, J=9.38 Hz), 3.92 (s, 2H) 3.65 (dt, 1H, J=5.9, 9.75), 3.49 (dt, 1H, J=9.64, 7.7), 2.0 to 2.3 (m, 8H), 1.72 to 1.94 (m, 8H), 1.65 (m, 2H)

EXAMPLE 4

(S)-1-[(3-(4-fluorophenyl)sulfonamido-1-adamantyl) amino]acetyl-2-cyano-pyrrolidine

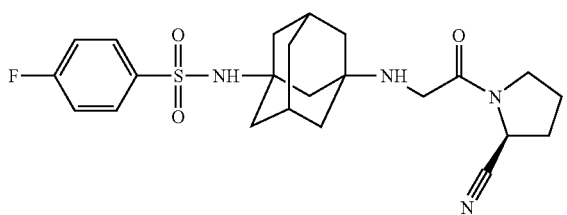

A solution of (S)-1-[(3-amino-1-adamantyl)amino]acetyl-2-cyano-pyrrolidine (150 mg, 0.5 mmol) in 3 mL of acetonitrile with triethylamine (105 μl, 0.75 mmol) was made and cooled to 0° C. in the freezer. The 4-fluorophenyl sulfonyl chloride was prepared in advance as a 0.5 M solution in dry THF. The sulfonyl chloride solution (1.5 mL, 0.75 mmol) was added drop wise to the stirring cooled amine solution and the reaction allowed to warm to room temperature overnight. The crude reaction mixture was analyzed by LC/MS and showed complete conversion to product. The crude reaction mixture was evaporated to dryness and diluted to 3 mL in 3/1 acetonitrile: water. The sample was purified by reverse phase HPLC with mass directed fractionation using an acetonitrile/ water gradient with TFA as a modifier. After lyophilization, 112 mg of the mono-TFA salt was isolated. 39% yield. $^1$H NMR (CD$_3$N, 400 MHz) δ 7.9 (dd, 2H, J=5.2, 9.9 Hz), 7.27 (d, 2H, J=8.8 Hz), 5.85 (s, 1H), 4.675 (t, 1H, J=5.75 Hz), 3.8 (s, 1H), 3.59 (dt, 1H, J=5.49, 9.7 Hz), 3.44 (dt, 1H, J=9.4, 7.7 Hz), 2.0 to 2.3 (m, 7H), 1.5 to 1.85 (m, 11H).

EXAMPLE 5

6-(3-(2-((S)-2-cyanopyrrolidin-1-yl)-2-oxoethylamino)-adamantylamino)nicotinonitrile

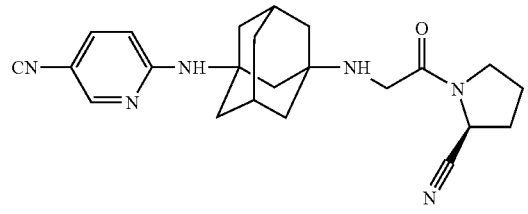

To a solution of (S)-1-[(3-amino-1-adamantyl)amino] acetyl-2-cyano-pyrrolidine (220 mg, 0.73 mmol) in 0.5 mL of DMF was added 2-chloro-5-cyanopyridine (350 mg, 2.53 mmol) with stirring. The reaction was heated to 90° C. and held at that temperature for 18 hrs. The reaction was analyzed by LC/MS and conversion to product was approximately 50%. The crude reaction mixture was dried under high vacuum for 3 hrs. and then purified by flash chromatography. The excess 2-chloro-5-cyanopyridine was eluted with dichloromethane and the 6-(3-(2-((S)-2-cyanopyrrolidin-1-yl)-2-oxoethylamino)-adamantylamino)-nicotinonitrile was eluted with 10% methanol/dichloromethane (66 mg, 22.4% yield) as a pale orange hygroscopic solid. $^1$H NMR (CD$_3$N, 400 MHz) δ 8.322 (d, 1H, J=1.5 Hz), 7.57 (dd, 1H, J=2.35, 8.98 Hz), 6.54 (d, 1H, J=8.98 Hz), 4.7 (dd, 1H, J=5.4, 6.0 Hz), 3.9 (d, 2H, J=2.28 Hz), 3.64 (dt, 1H, J=5.89, 9.74 Hz), 3.46 (dt, 1H, J=9.6, 7.7 Hz), 2.42 (m, 6H), 2.26 (m, 6H), 2.15 (m, 3H), 1.19 (m, 3H).

EXAMPLE 6

N'-(3-(2-((S)-2-cyanopyrrolidin-1-yl)-2-oxoethylamino)-adamantyl)-N,N-dimethyl-sulfamide

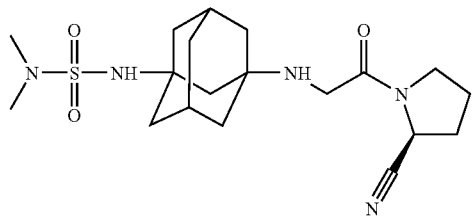

A solution of (S)-1-[(3-amino-1-adamantyl)amino]acetyl-2-cyano-pyrrolidine (150 m, 0.5 mmol) in 3 mL of acetonitrile with triethylamine (105 µl, 0.75 mmol) was made and cooled to 0° C. in the freezer. The dimethylsulfamoyl chloride was prepared in advance as a 0.5 M solution in dry THF. The sulfamoyl chloride solution (1.5 mL, 0.75 mmol) was added drop wise to the stirring cooled amine solution and the reaction allowed to warm to room temperature overnight. The crude reaction mixture was analyzed by LC/MS and showed complete conversion to product. The crude reaction mixture was evaporated to dryness and diluted to 3 mL in 3/1 acetonitrile: water. The sample was purified by reverse phase HPLC with mass directed fractionation using an acetonitrile/water gradient with TFA as a modifier. After lyophilization, 72 mg of the mono-TFA salt was isolated. 27% yield. $^1$H NMR (CD$_3$N, 400 MHz) δ 5.1 (bs, 1H), 4.69 (t, 1H, J=5.4 Hz), 3.874 (s, 2H), 3.62 (dt, 1H, J=5.6, 9.6 Hz), 3.44 (dt, 1H, J=9.8, 7.7 Hz), 2.77 (s, 1H), 2.7 (s, 6H) 2.08 to 2.35 (m, 9H), 1.58 to 1.9 (m, 9H)

EXAMPLE 7

1-(3-(2-((S)-2-cyanopyrrolidin-1-yl)-2-oxoethylamino)-adamantyl)-3-(4-fluorophenylsulfonyl)urea

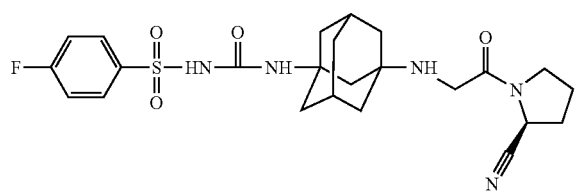

A solution of (S)-1-[(3-amino-1-adamantyl)amino]acetyl-2-cyano-pyrrolidine (60 mg, 0.2 mmol) in 1 mL of acetonitrile with triethylamine (56 µl, 0.4 mmol) was made and cooled to 0° C. in the freezer. The 4-fluorobenzene sulfonyl isocyanate was prepared in advance as a 0.3 M solution in dry THF. The sulfonyl isocyanate solution (1.0 mL, 0.3 mmol) was added drop wise to the stirring cooled amine solution and the reaction allowed to warm to room temperature overnight. The crude reaction mixture was analyzed by LC/MS and showed complete conversion to product. The crude reaction mixture was evaporated to dryness and diluted to 3 mL in 3/1 acetonitrile: water. The sample was purified by reverse phase HPLC with mass directed fractionation using an acetonitrile/water gradient with TFA as a modifier. After lyophilization, 20 mg of the mono-TFA salt was isolated. 20% yield.

EXAMPLES 8-9

Intermediate and Additional Active Compound

EXAMPLE 8

1-Amino-4-(dimethylaminosulfonylamino)bicyclo[2.2.2]octane

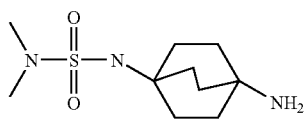

A solution of 1,4-diaminobicyclo[2.2.2]octane (7.01 g, 50 mmol)(produced as described in Example 24 below) and triethylamine (20 mL, 144 mmol) in anhydrous acetonitrile (150 mL) under nitrogen was treated with potassium carbonate (40 g, 290 mmol), cooled on an ice bath, and treated dropwise with dimethylsulfamoyl chloride (4.31 g, 30 mmol). The mixture was warmed to room temperature and stirred for 18 h, then diluted with methylene chloride (250 mL) and treated with DOWEX® 550A-OH hydroxide resin (20 g which was first rinsed with acetonitrile and methylene chloride before addition). The solution was stirred 1 h and filtered through Celite® and the filtrate concentrated in vacuo. The residue was dissolved in methylene chloride and loaded onto a silica gel column (~400 cc) and eluted first with 7% methanol/methylene chloride to afford 1,4-bis(dimethylaminosulfonylamino)-bicyclo[2.2.2]octane (2.42 g), then eluted with 90:9:1 methylene chloride/-ethanol/ammonium hydroxide to afford 1-amino-4-(dimethylaminosulfonylamino)bicyclo[2.2.2]octane (3.31 g), then with 60:30:10 methylene chloride/-methanol/ammonium hydroxide to afford recovered 1,4-diaminobicyclo[2.2.2]-octane (3.90 g). The yield of subject material was 60% based on recovered starting material. [M+H]$^+$=248.4. $^1$H NMR (CDCl$_3$) δ 4.22 (br s, 1H), 2.73 (s, 6H), 1.88 (m, 6H), 1.60 (m, 6H).

EXAMPLE 9

(S)-2-Cyano-1-(1-(dimethylaminosulfonyl-amino)bicyclo[2.2.2]oct-4-yl)aminoacetyl)pyrrolidine

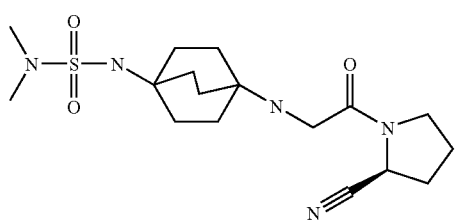

A mixture of 1-amino-4-(dimethylaminosulfonylamino)bicyclo[2.2.2]octane (3.66 g, 14.8 mmol)(produced as described in Example 8 above), potassium carbonate (20.7 g, 150 mmol), and potassium iodide (0.50 g, 3.0 mmol) in anhydrous N,N-dimethylformamide (60 mL) under nitrogen was treated with (S)-1-chloroacetyl-2-cyanopyrrolidine (2.68 g, 15.5 mmol) and stirred at room temperature for 18 h, then combined with methylene chloride (180 mL) and triethylamine (8 mL). After a few minutes of stirring, the mixture was filtered through Celite® and the filtrate concentrated in vacuo (exhaustively to remove DMF) to a crude pale yellow solid. This was dissolved in acetonitrile (20 mL), diluted with ether (25 mL), and stirred for awhile to afford a precipitate, which was cooled and filtered. The solid was rinsed with several portions of cold 3:1 ether/acetonitrile and dried in vacuo to afford 3.56 g of white solid. The combined filtrates were concentrated in vacuo and chromatographed on silica gel (~200 cc) and eluted with 7% methanol/ethyl acetate, then with 7% methanol/methylene chloride to afford additional subject material (1.97 g). The total yield of (S)-2-cyano-1-(1-(dimethylaminosulfonylamino)bicyclo[2.2.2]oct-4-yl)aminoacetyl)pyrrolidine was 5.53 g (97%). [M+H]$^+$=384.4. $^1$H NMR (CDCl$_3$) δ 4.70-4.82 (m, 1H), 4.08 (s, 1H), 3.30-3.70 (m, 4H), 2.75 (s, 6H), 2.00-2.35 (m, 4H), 1.90 (m, 6H), 1.65 (m, 6H).

EXAMPLES 10-19

Additional Examples of Active Compounds

EXAMPLE 10

(S)-2-Cyano-1-(1-(4-fluorobenzenesulfonyl-amino) bicyclo [2.2.2]oct-4-yl)aminoacetyl)pyrrolidine

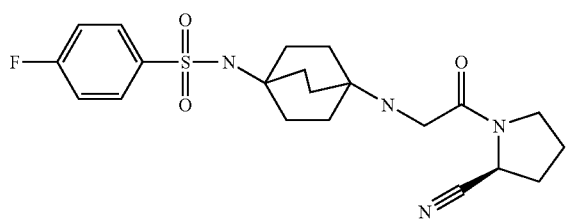

An ice-cooled solution of (S)-(1-(1-aminobicyclo[2.2.2] oct-4-yl)aminoacetyl)-2-cyanopyrrolidine (83 mg, 0.30 mmol) and triethylamine (0.21 mL, 1.5 mmol) in anhydrous methylene chloride (1.5 mL) was treated dropwise with 4-fluorobenzenesulfonyl chloride (64 mg, 0.33 mmol) in anhydrous methylene chloride (0.5 mL), and the mixture was stirred at room temperature for 2.5 h, then concentrated in vacuo. The residue was redissolved in methylene chloride and loaded onto a silica gel column (~15 cc) and eluted first with 2%, then 4%, then 6% methanol/methylene chloride to afford 87 mg (67%) of (S)-2-cyano-1-(1-(4-fluorobenzenesulfonylamino)bicyclo[2.2.2]oct-4-yl)aminoacetyl)pyrrolidine as a white foam. [M+H]$^+$=435.4. $^1$H NMR (CDCl$_3$) δ 7.87 (dd, 2H, J=9 Hz, 6 Hz), 7.15 (t, 2H, J=9 Hz), 4.71-4.76 (m, 1H), 4.56 (s, 1H), 3.20-3.70 (m, 4H), 2.05-2.35 (m, 4H), 1.78 (m, 6H), 1.56 (m, 6H).

EXAMPLE 11

(S)-2-Cyano-1-(1-(4-cyanobenzenesulfonyl-amino) bicyclo[2.2.2]oct-4-yl)aminoacetyl)pyrrolidine and HCl salt

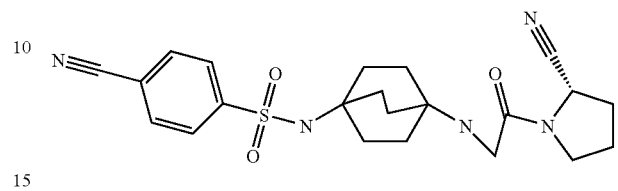

An ice-cooled solution of (S)-(1-(1-aminobicyclo[2.2.2] oct-4-yl)aminoacetyl)-2-cyanopyrrolidine (83 mg, 0.30 mmol) and triethylamine (0.21 mL, 1.5 mmol) in anhydrous methylene chloride (2.0 mL) was treated dropwise with 4-cyanobenzenesulfonyl chloride (66.5 mg, 0.33 mmol) in anhydrous methylene chloride (1.0 mL), and the mixture was stirred at 5° C. for 4 h, then concentrated in vacuo. The residue was redissolved in methylene chloride and loaded onto a silica gel column (~20 cc) and eluted with 5%, then 10% methanol/ethylacetate to afford 64 mg (48%) of (S)-2-cyano-1-(1-(4-cyanobenzenesulfonylamino)bicyclo-[2.2.2]oct-4-yl)aminoacetyl)pyrrolidine as a white solid. [M+H]$^+$=442.4. $^1$H NMR (CDCl$_3$) δ 7.95-8.01 (m, 2H), 7.76-7.82 (m, 2H), 4.78-4.84 (m, 1H), 4.73 (br s, 1H), 3.20-3.70 (m, 4H), 2.05-2.35 (m, 4H), 1.80 (m, 6H), 1.60 (m, 6H).

A solution/suspension of the subject free base (64 mg, 0.145 mmol) in anhydrous THF (1 mL) was treated with 0.25N ethereal HCl (0.7 mL, 0.175 mmol), diluted with ether, stirred a few minutes, filtered, and the solid was rinsed with ether, collected, and dried in vacuo to afford 51 mg (74%) of the subject HCl salt as a white solid.

EXAMPLE 12

(S)-2-Cyano-1-(1-(dimethylaminosulfonyl-amino) bicyclo [3.2.1]oct-3-yl)aminoacetyl)pyrrolidine

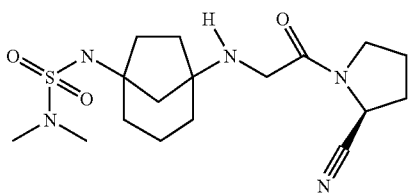

A cooled (5° C.) solution of (S)-(1-(1-aminobicyclo[3.2.1] oct-3-yl)aminoacetyl)-2-cyanopyrrolidine (69 mg, 0.35 mmol) in anhydrous methylene chloride (2 mL) under nitrogen was treated with potassium carbonate (210 mg, 1.5 mmol), then with dimethylsulfamoyl chloride (50.3 mg, 0.35 mmol). The mixture was stirred 6 h at 5° C., treated with more dimethylsulfamoyl chloride (35 mg, 0.25 mmol), stirred another hour, treated with triethylamine (0.14 mL, 1.0 mmol), then stirred at room temperature for 15 h. The mixture was filtered through Celite® and the filtrate concentrated in vacuo. The residue was dissolved in methylene chloride and loaded onto a silica gel column (~20 cc) and eluted with 7% methanol/ethyl acetate, then 7% methanol/methylene chloride to afford (S)-2-cyano-1-(1-(dimethylaminosulfonylamino)bicyclo[3.2.1]oct-3-yl)aminoacetyl)pyrrolidine 28 mg, 29%) as a colorless glass. [M+H]⁺=384.4. ¹H NMR (CDCl₃) δ 4.70-4.85 (m, 1H), 4.59 (s, 1H), 3.35-3.70 (m, 4H), 2.75 (s, 6H), 2.10-2.30 (m, 4H), 1.90-2.02 (m, 2H), 1.63-1.85 (m, 5H), 1.40-1.63 (m, 5H).

EXAMPLE 13

(S)-2-Cyano-1-(1-(dimethylaminosulfonyl-amino) bicyclo [3.1.1]hept-3-yl)aminoacetyl)pyrrolidine

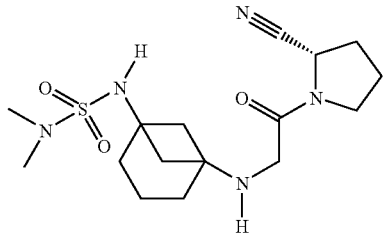

A cooled (5° C.) solution of (S)-(1-(1-aminobicyclo[3.1.1] hept-3-yl)aminoacetyl)-2-cyanopyrrolidine (52.5 mg, 0.20 mmol), triethylamine (0.14 mL, 1.0 mmol), and potassium carbonate (0.30 g, 2.2 mmol) in anhydrous acetonitrile (1.5 mL) under nitrogen was treated with dimethylsulfamoyl chloride (36 mg, 0.25 mmol), stirred 1 h at 5° C. and 3 h at room temperature, and diluted with methylene chloride (6 mL). The mixture was filtered and the filtrate concentrated in vacuo, redissolved in methylene chloride, and loaded onto a silica gel column (~20 cc), then eluted with 2%, 3%, 4%, and 5% methanol/methylene chloride to afford (S)-2-cyano-1-(1-(dimethylamino-sulfonylamino)bicyclo[3.1.1]hept-3-yl) aminoacetyl)-pyrrolidine (39 mg, 53%) as a colorless glass. [M+H]⁺=370.3. ¹H NMR (CDCl₃) δ 4.70-4.90 (m, 2H), 3.30-3.70 (m, 4H), 2.73 (s, 6H), 2.00-2.30 (m, 8H), 1.70-1.90 (m, 6H).

EXAMPLE 14

(S)-2-Cyano-1-(1-(4-fluorobenzenesulfonyl-amino) bicyclo[3.2.1]oct-3-yl)aminoacetyl)pyrrolidine

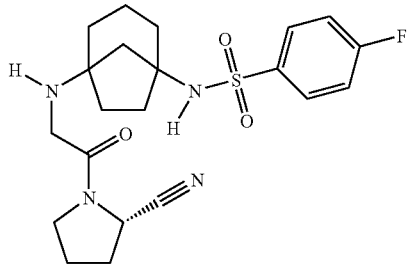

A cooled (5° C.) solution of (S)-(1-(1-aminobicyclo[3.2.1] oct-3-yl)aminoacetyl)-2-cyanopyrrolidine (55.3 mg, 0.20 mmol) in anhydrous methylene chloride (1 mL) under nitrogen was treated with triethylamine (0.14 mL, 1.0 mmol), then with 4-fluorobenzenesulfonyl chloride (59 mg, 0.30 mmol), and stirred 2.5 h at room temperature. The mixture was concentrated in vacuo and the residue redissolved in methylene chloride and loaded onto a silica gel column (~15 cc), then eluted with 2% methanol/ethyl acetate, then 7% methanol/ ethyl acetate to afford (S)-2-cyano-1-(1-(4-fluorobenzenesulfonylamino)bicyclo[3.2.1]oct-3-yl)-aminoacetyl)pyrrolidine (57 mg, 66%) as a white foam. [M+H]⁺=435.4. ¹H NMR (CDCl₃) δ 7.89 (m, 2H), 7.16 (m, 2H), 4.90-5.00 (m, 1H), 4.70-4.78 (m, 1H), 3.30-3.65 (m, 4H), 2.05-2.35 (m, 4H), 1.40-1.90 (m, 12H).

EXAMPLE 15

(S)-2-Cyano-1-(1-(4-fluorobenzenesulfonyl-amino) bicyclo [3.1.1]hept-3-yl)aminoacetyl)pyrrolidine

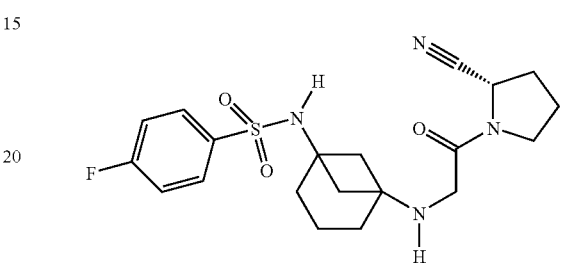

A cooled (5° C.) solution of (S)-(1-(1-aminobicyclo[3.1.1] hept-3-yl)aminoacetyl)-2-cyanopyrrolidine (52.5 mg, 0.20 mmol) in anhydrous methylene chloride (1.5 mL) under nitrogen was treated with triethylamine (0.14 mL, 1.0 mmol), then with 4-fluorobenzenesulfonyl chloride (43 mg, 0.22 mmol) in methylene chloride (0.5 mL), and stirred 1.5 h at 5° C. The mixture was concentrated in vacuo and the residue redissolved in methylene chloride and loaded onto a silica gel column (~15 cc), then eluted with 3% methanol/methylene chloride, then 5% methanol/methylene chloride to afford (S)-2-cyano-1-(1-(4-fluorobenzenesulfonylamino)bicyclo [3.1.1]-hept-3-yl)aminoacetyl)pyrrolidine (80 mg, 95%) as a white foam. [M+H]⁺=421.3. ¹H NMR (CDCl₃) δ 7.87 (dd, 2H, J=9 Hz, 6 Hz), 7.16 (t, 2H, J=9 Hz), 5.35-5.50 (m, 1H), 4.68-4.77 (m, 1H), 3.25-3.65 (m, 4H), 2.05-2.35 (m, 4H), 1.85-2.00 (m, 5H), 1.55-1.80 (m, 5H).

EXAMPLE 16

1-[(3-(4-fluorophenyl)sulfonamido-1-adamantyl) amino]-1-(thiazolididn-3-yl)ethanone

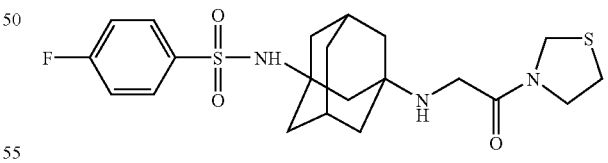

To a cooled with ice bath solution of the 2-(3-aminoadamantyl)-1-(thiazolidin-3-yl)ethanone (100 mg, 0.339 mmol) in 4 ml of THF and triethylamine (1 ml) 4-fluorobenzenesulfonyl chloride (80 mg, 0.41 mmol) was added. The reaction mixture was stirred for 18 hours then checked by LCMS (M+1=454). The crude was concentrated and purified by mass directed fractionation with an acetonitrile/water gradient and TFA as a modifier. After lyophilization of the fractions 63 mg of the mono TFA salt was isolated. (32.8% yield). ¹H NMR (CD₃CN, 400 MHz), δ 7.955 to 7.90 (m, 2H), 7.29 (t, 2H, J=8.4), 5.9 (b, 1H), 4.54 (s, 1H), 4.49 (s, 1H), 3.88 (s, 1H), 3.865 (s, 1H), 3.8 to 3.75 (m, 1H), 3.71 (t, 1H, J=6.16), 3.151 (t, 1H, J=6.12), 3.05 (t, 1H, J=6.16), 2.25 (b, 2H), 2.02 (s, 2H), 2.01 to 1.93 (m, 4H), 1.84 to 1.65 (m, 7H), 1.53 to 1.50 (m, 2H).

EXAMPLE 17

1-[(3-(4-fluorophenyl)sulfonamido-1-adamantyl)amino]acetyl-3,3-difluoropyrrolidine

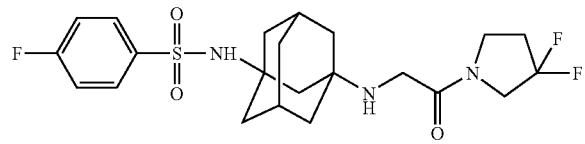

To a cooled with ice bath solution of the 2-(3-aminoadamantyl)-1-(3,3-difluoropyrrolidin-1-yl)ethanone (80 mg, 0.26 mmol) in 4 ml of THF and triethylamine (1 ml) 4-fluorobenzenesulfonyl chloride (50 mg, 0.26 mmol) was added. The reaction mixture was stirred for 18 hours then checked by LCMS and showed complete conversion to product M+1=472. Then crude material was concentrated and purified by column silica gel chromatography using DCM/MeOH as eluting solvent to afford 50 mg of 1-[(3-(4-fluorophenyl)sulfonamido-1-adamantyl)amino]acetyl-3,3-difluoropyrrolidine (42% yield). $^1$H NMR (CD$_3$CN, 400 MHz), δ 7.951 to 7.896 (m, 2H), 7.285 (t, 2H, J=8.793), 6.006 (s, 1H), 3.902 to 3.621 (m, 6H), 2.572 to 2.344 (m, 3H), 2.243 (b, 2H), 1.988 (s, 1H), 1.831 (s, 4H), 1.798 to 1.648 (m, 5H), 1.523 (b, 2H).

EXAMPLE 18

1-[(3-(4-fluorophenyl)sulfonamido-1-adamantyl)amino]acetyl-4-cyanothiazolidine

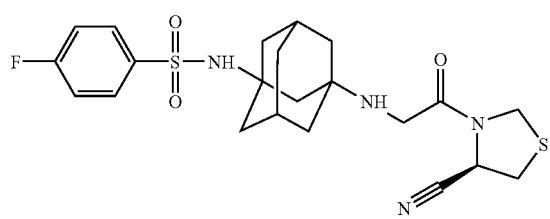

This compound was synthesized the same way as described for 1-[(3-(4-fluorophenyl)sulfonamido-1-adamantyl)amino]acetyl-3,3-difluoropyrrolidine. The crude compound was concentrated and purified by mass directed fractionation with an acetonitrile/water gradient and TFA as a modifier. MS (ESI) m/z=479 (M+H)$^+$. 9% yield.

EXAMPLES 19-22

Additional Examples of Active Compounds

EXAMPLE 19

(S)-1-[(3-aminosulfamoyl-1-adamantyl)-amino]acetyl-2-cyanopyrrolidine

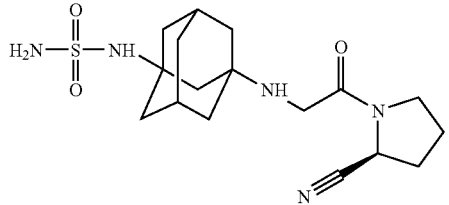

To a solution of (S)-1-[3-(tert-butyl-methylcarbamoylsulfamoyl-1-adamantyl)-amino]acetyl-2-cyanopyrrolidine (200 mg 0.41 mmol) in 7 ml of methylene chloride, 2 ml of TFA added. The reaction mixture was stirred for 2 hours. The crude was checked by LCMS and showed complete conversion to product M+1=382. The crude was concentrated and purified by mass directed fractionation with an acetonitrile/water gradient and TFA as a modifier. After lyophilization of the fractions 160 mg of the mono TFA salt was isolated. (77.7% yield). 1H NMR (CD3CN, 400 MHz), δ5.40 (b, 2H), 4.72 (t, 1H, J=5.56 Hz), 3.92 (s, 2H), 3.65 (dt, 1H, J=4.9, J=9.38), 3.47 (dt, 1H, J=7.62, J=9.38), 2.78 (b, 2H), 2.35 (t, 2H, J=2.3), 2.26 to 2.08 (m, 7H), 2.0 to 1.82 (m, 3H), 1.67 to 1.55 (m, 2H).

EXAMPLE 20

N'-(3-(2-((S)-2-cyanopyrrolidin-1-yl)-2-oxoethylamino)-adamantyl)-sulfonylpyrrolidine

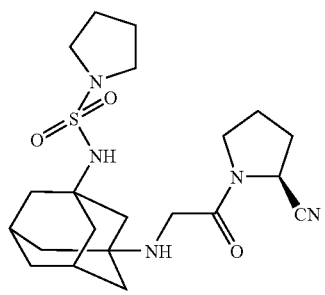

A solution of the N'-(3-(2-((S)-2-cyanopyrrolidin-1-yl)-2-oxoethylamino)-adamantyl)-sulfonyloxazolidinone (50 mg, 0.11 mmole) in 1 ml of acetonitrile with triethylamine (28 ul, 0. 2 mmole). The pyrrolidine (10 ul, 0.12 mmole) was added to the solution which was heated to 90° C. for 18 hrs. with shaking at 180 rpm. The crude was checked by LCMS and showed complete conversion to product M+1=436. The crude was evaporated to dryness and diluted to 1 mls in 3/1 acetonitrile: water. The sample was purified by mass directed fractionation with an acetonitrile/water gradient and TFA as a modifier. After lyophilization of the fractions 20 mg of the mono TFA salt was isolated. 33% yield. $^1$H NMR (CD$_3$N, 400 MHz) δ 5.19 (bs, 1H), 4.71 (t, 1H, J=5.3 Hz), 3.90 (s, 2H), 3.64 (m, 1H), 3.47 (q, 1H, J=8.0 Hz), 3.23 (s, 4H), 2.35 (bs, 4H), 2.25 (m, 2H), 2.18 (m, 4H), 1.89 (m, 9H), 1.6 (s, 2H)

EXAMPLE 21

N'-(3-(2-((S)-2-cyanopyrrolidin-1-yl)-2-oxoethylamino)-adamantyl)-N-(4-fluorobenzyl) sulfamide

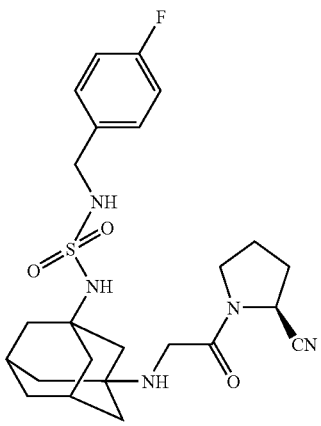

A solution of the N'-(3-(2-((S)-2-cyanopyrrolidin-1-yl)-2-oxoethylamino)-adamantyl)-sulfonyloxazolidinone (50 mg, 0.11 mmole) in 1 ml of acetonitrile with triethylamine (28 ul, 0. 2 mmole). The 4-fluorobenzylamine (14 ul, 0.12 mmole) was added to the solution which was heated to 90° C. for 18 hours with shaking at 180 rpm. The crude was checked by LCMS and showed complete conversion to product M+1=490. The crude was evaporated to dryness and diluted to 1 mls in 3/1 acetonitrile: water. The sample was purified by mass directed fractionation with an acetonitrile/water gradient and TFA as a modifier. After lyophilization of the fractions 20 mg of the mono TFA salt was isolated. 30% yield. $^1$H NMR (CD$_3$N, 400 MHz) δ 7.41 (t, 2H, J=6.4 Hz), 7.12 (t, 2H, J=8.9 Hz), 4.71 (t, 1H, J=5.2 Hz), 4.14 (s, 2H), 3.90 (s, 2H), 3.62 (m, 1H), 3.46 (q, 1H, J=8.2 Hz), 2.23 (m, 6H), 2.14 (m, 2H), 1.89 (m, 9H), 1.62 (s, 2H)

EXAMPLE 22

N'-(3-(2-((S)-2-cyanopyrrolidin-1-yl)-2-oxoethylamino)-adamantyl)-N-(4-fluorophenethyl) sulfamide

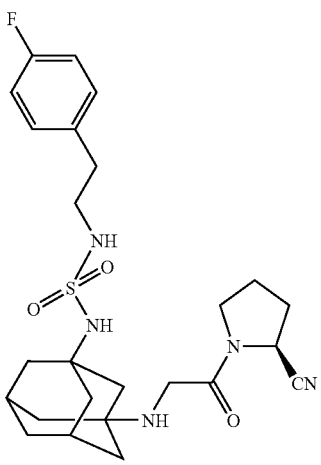

A solution of the N'-(3-(2-((S)-2-cyanopyrrolidin-1-yl)-2-oxoethylamino)-adamantyl)-sulfonyloxazolidinone (50 mg, 0.11 mmole) in 1 ml of acetonitrile with triethylamine (28 ul, 0.2 mmole). The 4-fluorophenethylamine (16 ul, 0.12 mmole) was added to the solution which was heated to 90° C. for 18 hrs. with shaking at 180 rpm. The crude was checked by LCMS and showed complete conversion to product M+1=504. The crude was evaporated to dryness and diluted to 1 mls in 3/1 acetonitrile: water. The sample was purified by mass directed fractionation with an acetonitrile/water gradient and TFA as a modifier. After lyophilization of the fractions 20 mg of the mono TFA salt was isolated. 30% yield. $^1$H NMR (CD$_3$N, 400 MHz) δ 7.30 (t, 2H, J=6.2 Hz), 7.08 (t, 2H, J=8.9 Hz), 4.70 (t, 1H, J=5.3 Hz), 3.89 (s, 2H), 3.63 (m, 1H), 3.46 (q, 1H, J=9.2 Hz), 3.19 (bs, 2H), 2.85 (t, 2H, J=6.8 Hz), 2.32 to 2.20 (m, 6H), 2.18 (m, 2H), 1.86 (m, 9H), 1.59 (s, 2H)

EXAMPLES 23-33

Synthesis of Intermediate or Precursor Compounds

EXAMPLE 23

1,4-Dicarboxybicyclo[2.2.2]octane

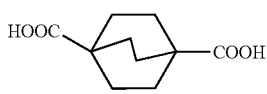

A stirred solution of 1,4-dicarbomethoxybicyclo[2.2.2]octane (31.7 g, 0.14 mole) in tetrahydrofuran (200 mL) and isopropanol (70 mL) was treated with a solution of lithium hydroxide hydrate (17.7 g, 0.42 mole) in water (200 mL), and the mixture was heated to 6°-70° C. for 2.5 h with stirring. The organic solvents were removed in vacuo, and the alkaline aqueous solution was filtered, then the filtrate was cooled on an ice bath and acidified with concentrated hydrochloric acid (40 mL). The solid was filtered, rinsed with cold water, and partially air dried overnight, then further dried under vacuum, triturated from acetonitrile, and redried in vacuo to afford 27.19 g (98%) of subject material as a white solid. No MS could be obtained. $^1$H NMR (d6-DMSO) δ 12.09 (br s, 2H), 1.66 (s, 12H).

EXAMPLE 24

1,4-Diaminobicyclo[2.2.2]octane dihydrochloride

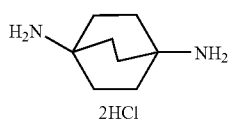

A suspension of 1,4-dicarboxybicyclo[2.2.2]octane (9.91 g, 50 mmol) in toluene (225 mL) was azeotroped under a Dean-Stark trap to dryness, then cooled to room temperature under nitrogen and treated with triethylamine (20 mL, 143 mmol) and diphenylphosphoryl azide (33.0 g, 120 mmol). The solution was slowly and cautiously warmed to 80° C. (some exotherm and much evolution of gas observed) and stirred at 80°-90° C. for 3 h, then concentrated in vacuo to remove toluene and the residue cooled on an ice bath and treated with 6N hydrochloric acid (150 mL, 900 mmol). The bath was removed and the mixture stirred at room temperature for 3 h, then partially concentrated to remove most water. Acetonitrile (600 mL) was added, and the suspension was cooled for an hour in a refrigerator, filtered, and the solid rinsed with acetonitrile and dried in vacuo to afford 9.31 g (87%) of subject material as a white solid. [M+H]$^+$=141.3. $^1$H NMR (d6-DMSO) δ 8.24 (br s, 6H), 1.81 (s, 12H).

EXAMPLE 25

1,3-Dicarbomethoxybicyclo[3.2.1]octane

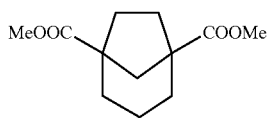

A cooled (−67° C.) solution of dry diisopropylamine (11.0 mL, 78 mmol) in anhydrous THF (60 mL) in a 3-neck 500 mL round bottom flask equipped with magnetic stirring, addition funnel, and gas inlet/thermometer was treated via syringe with 2.4N n-butyllithium/hexane (30 mL, 72 mmol) at a rate to keep the pot temperature <−50° C., warmed to 0° C. for 5 minutes, then recooled (−67° C.). 1,3-Dimethyl-3,4,5,6-tetrahydro-2(1H)-pyrimidinone (DMPU, 36.3 mL, 300 mmole, dried over molecular seives) was added dropwise so as to keep pot temp <−60° C., then a solution of dimethyl cyclohexane-1,3-dicarboxylate (12.01 g, 60 mmol) in anhydrous THF (20 mL) was likewise added dropwise. After 1 h at −67° C., a solution of 1-bromo-2-chloroethane (12.05 g, 84 mmol) in anhydrous THF (15 mL) was added dropwise so as to keep pot temp <−50° C., and the mixture was warmed to room temperature over 1.5 h and stirred at room temperature for 18 h, then cooled on an ice bath and quenched with saturated aqueous ammonium chloride (50 mL). The organic solvent was removed in vacuo and the aqueous residue was extracted with 9:1 hexane/ethyl acetate (150 mL, 100 mL, 2×50 mL). The combined organic extracts were washed with water (100 mL), dried (MgSO$_4$), and concentrated in vacuo. The residue was dissolved in methylene chloride and passed through a pad of alumina in a 60 mL fritted glass funnel (eluted with methylene chloride) to afford 15.36 g (97% of theoretical) of a pale yellow oil which was essentially the desired intermediate with minor impurities.

A solution of 1-(2-chloroethyl)-1,3-dicarbomethoxycyclohexane (all of semi-purified from 60 mmol dimethyl cyclohexane-1,3-dicarboxylate) and DMPU (36.3 mL, 300 mmol) in anhydrous THF (150 mL) under nitrogen in a 500 mL 3-neck flask equipped with magnetic stirring, addition funnel, and gas inlet/thermometer was cooled to −67° C. Meanwhile, a cooled (−67° C.) solution of dry diisopropylamine (11.0 mL, 78 mmol) in anhydrous THF (75 mL) under nitrogen was treated via syringe with 2.4N n-butyllithium/hexane (30 mL, 72 mmol), the mixture was warmed to 0° C. for 5 min, then recooled (−67° C.). The LDA solution was cannulated in portions (~6) into the other solution at a rate to keep pot temperature <−60° C., then the mixture was stirred at −67° C. for 30 min, warmed to room temperature over 1.5 h, then stirred at room temperature for 18 h, cooled on an ice bath and quenched with saturated aqueous ammonium chloride (50 mL). The organic solvent was removed in vacuo and the aqueous residue was extracted with 9:1 hexane/ethyl acetate (150 mL, 100 mL, 2×50 mL). The combined organic extracts were washed with water (100 mL), dried (MgSO$_4$), and concentrated in vacuo. The residue was dissolved in methylene chloride and passed through a pad of alumina in a 60 mL fritted glass funnel (eluted with methylene chloride) to afford crude subject material (9.52 g) as a pale yellow oil. Chromatography on silica gel (~400 cc) eluted with 40%, then 50% methylene chloride/hexane, then methylene chloride alone, then 10% ethyl acetate/methylene chloride afforded 8.32 g (61% for two steps from dimethyl cyclohexane-1,3-dicarboxylate) purified subject material as a very pale yellow oil. [M+H]$^+$=226.9. $^1$H NMR (CDCl$_3$) δ 3.66 (s, 6H), 2.20-2.30 (m, 1H), 2.00-2.10 (m, 2H), 1.70-1.80 (m, 5H), 1.55-1.65 (m, 4H).

EXAMPLE 26

1,3-Dicarboxybicyclo[3.2.1]octane

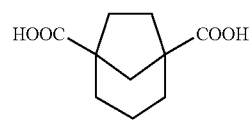

A stirred solution of 1,3-dicarbomethoxybicyclo[3.2.1]octane (8.26 g, 36.5 mmol) in tetrahydrofuran (50 mL) and isopropanol (16 mL) was treated with a solution of lithium hydroxide hydrate (4.20 g, 100 mmol) in water (50 mL), and the mixture was heated to 60°-70° C. for 2 h with stirring. The organic solvents were removed in vacuo, and the alkaline aqueous solution was cooled on an ice bath and acidified with concentrated hydrochloric acid (10 mL). The solid was filtered, rinsed with cold water, and partially air dried overnight, then further dried under vacuum, triturated from acetonitrile, and redried in vacuo to afford 6.25 g (86%) of subject material as a white solid. No MS could be obtained. ¹H NMR (CDCl₃+ drop d6-DMSO) δ 2.15-2.25 (m, 1H), 1.95-2.05 (m, 2H), 1.40-1.70 (m, 9H).

EXAMPLE 27

1,3-Diaminobicyclo[3.2.1]octane dihydrochloride

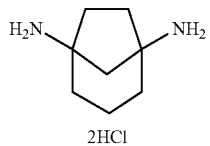

2HCl

A suspension of 1,3-dicarboxybicyclo[3.2.1]octane (6.15 g, 31 mmol) in toluene (150 mL) was azeotroped under a Dean-Stark trap to dryness, then cooled to room temperature under nitrogen and treated with triethylamine (12.2 mL, 87.5 mmol) and diphenylphosphoryl azide (20.4 g, 74 mmol). The solution was slowly and cautiously warmed to 80° C. (some exotherm and much evolution of gas observed) and stirred at 80°-90° C. for 3 h, then concentrated in vacuo to remove toluene and the residue cooled on an ice bath and treated with 6N hydrochloric acid (60 mL, 360 mmol). The bath was removed and the mixture stirred at room temperature for 3 h, then partially concentrated to remove most water. Acetonitrile (150 mL) was added, and the suspension was cooled for an hour in a refrigerator, filtered, and the solid rinsed with acetonitrile and dried in vacuo to afford 5.25 g (79%) of subject material as a white solid. [M+H]⁺=141.3. ¹H NMR (d6-DMSO) δ 8.55 (br s, 6H), 2.23 (m, 1H), 1.91 (m, 2H), 1.55-1.75 (m, 9H).

EXAMPLE 28

1,3-Dicarbomethoxybicyclo[3.1.1]heptane

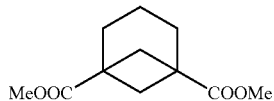

A cooled (−67° C.) solution of dry diisopropylamine (3.65 mL, 26 mmol) in anhydrous THF (20 mL) under nitrogen was treated via syringe with 2.5N n-butyllithium/hexane (9.6 mL, 24 mmol), warmed to 0° C. for 5 min, then recooled (−67° C.). DMPU (12.1 mL, 100 mmol) was added dropwise via addition funnel so as to keep pot temp <−60° C., then a solution of dimethyl cyclohexane-1,3-dicarboxylate (4.00 g, 20 mmol) in anhydrous THF (10 mL) was likewise added dropwise. After 1 h at −67° C., diiodomethane (7.23 g, 27 mmol) in THF (10 mL) was added dropwise, then the mixture was warmed to room temperature over 1 h stirred 1 h, cooled on an ice bath, and quenched with saturated aqueous ammonium chloride (20 mL). The organic solvents were removed in vacuo and water (30 mL) was added, and the aqueous was extracted with hexane (100 mL, then 2×50 mL). The combined organic extracts were washed with water (75 mL), dried (MgSO₄), and concentrated in vacuo, then dissolved in methylene chloride and passed through a pad of alumina in a fritted (30 mL) funnel. The concentrated filtrate was chromatographed on silica gel (~200 cc, eluted with 1:1 hexane/methylene chloride) to afford 4.65 g (68%) of 1-iodomethyl-1,3-dicarbomethoxycyclohexane as a colorless oil.

The above intermediate (4.59 g, 13.5 mmol) and DMPU (7.25 mL, 60 mmol) in anhydrous THF (30 mL) under nitrogen was cooled to −67° C. Meanwhile, a cooled (−67° C.) solution of dry diisopropylamine (2.6 mL, 18 mmol) in anhydrous THF (20 mL) under nitrogen was treated via syringe with 2.4N n-butyllithium/-hexane (6.25 mL, 15 mmol), warmed to 0° C. for 5 minutes, and recooled (−67° C.). The LDA solution was transferred via cannula in portions into the other solution at a rate to keep the pot temperature <−60° C., and the combined solution was stirred at −67° C. for 30 minutes, warmed to room temperature over 75 minutes, and stirred 4 h at room temperature. The mixture was cooled on an ice bath and quenched with saturated aqueous ammonium chloride (20 mL), then partially concentrated in vacuo to remove organics and extracted with hexane (3×50 mL). The combined extracts were washed with water (50 mL), dried (MgSO₄), and concentrated in vacuo, dissolved in methylene chloride and filtered through a pad of alumina in a 30 mL fritted glass funnel. The concentrated filtrate was chromatographed on silica gel (~120 cc, eluted with 10% ethyl acetate/hexane) to afford 1.97 g (69%) of subject material as a colorless oil. [M+H]⁺=213.2. ¹H NMR (CDCl₃) δ 3.66 (s, 6H), 2.45-2.55 (m, 2H), 1.75-2.00 (m, 8H).

EXAMPLE 29

1,3-Dicarboxybicyclo[3.1.1]heptane

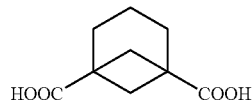

A stirred solution of 1,3-dicarbomethoxybicyclo[3.1.1] heptane (1.90 g, 8.95 mmol) in tetrahydrofuran (25 mL) and isopropanol (8 mL) was treated with a solution of lithium hydroxide hydrate (2.1 g, 50 mmol) in water (25 mL), and the mixture was heated to 60°-70° C. for 3 h with stirring. The organic solvents were removed in vacuo, and the alkaline aqueous solution was cooled on an ice bath and acidified with 6N hydrochloric acid (10 mL). The solid was filtered, rinsed with cold water, and partially air dried overnight, then further dried under vacuum to afford 6.25 g (86%) of subject material as a white solid. No MS could be obtained. ¹H NMR (CDCl₃) δ 2.40-2.50 (m, 2H), 1.90-2.00 (m, 4H), 1.80-1.90 (m, 2H), 1.70-1.80 (m, 2H).

EXAMPLE 30

1,3-Diaminobicyclo[3.1.1]heptane dihydrochloride

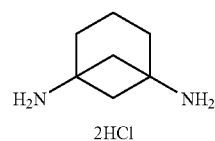

2HCl

A suspension of 1,3-dicarboxybicyclo[3.1.1]heptane (1.00 g, 5.43 mmol) in anhydrous toluene (35 mL) under nitrogen was treated with triethylamine (2.65 mL, 19 mmol) and diphenylphosphoryl azide (3.72 g, 13.5 mmol) and warmed to 80° C. and stirred at 80-90° C. for 3 h. The solution was concentrated in vacuo, cooled on an ice bath, and treated with 6N HCl (16 mL). The mixture was stirred at room temperature for 16 h, extracted with ether (2×25 mL), and concentrated in vacuo, then the residue was triturated from acetonitrile and dried to afford 560 mg (52%) of the subject material as a white solid. [M+H]$^+$=127.5.

$^1$H NMR (d6-DMSO) δ 8.66 (br s, 6H), 2.30-2.40 (m, 2H), 1.90-2.00 (m, 2H), 1.70-1.90 (m, 6H).

EXAMPLE 32

General Procedure for Generating Diamine Free Base From Dihydrochloride Salt: 1,4-Diaminobicyclo[2.2.2]octane DOWEX® 550A-OH hydroxide resin (Aldrich, 75 g) was suspended in methanol, filtered, rinsed with methanol, and partially air dried. A portion of 1,4-diamino-bicyclo[2.2.2]octane dihydrochloride (10 g, 46.8 mmol) was taken up in methanol (200 mL), then treated with the above hydroxyl resin and stirred for 30 min (making sure all white clumps were dissolved). The mixture was filtered, the resin rinsed with methanol, and the filtrate concentrated in vacuo to afford 6.46 g (98%) of 1,4-diaminobicyclo[2.2.2]octane free base as a white solid (caution: compound readily carbonates in air and must be stored under nitrogen).

EXAMPLE 32

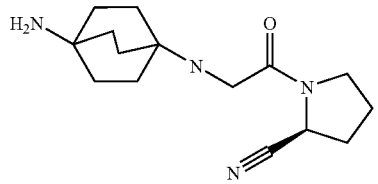

(S)-(1-(1-Aminobicyclo[2.2.2]oct-4-yl)aminoacetyl)-2-cyanopyrrolidine

A solution of 1,4-diaminobicyclo[2.2.2]octane free base (1.07 g, 7.6 mmol) and potassium carbonate (4.5 g, 32.6 mmol) in anhydrous N,N-dimethylformamide (DMF, 15 mL) under nitrogen was treated with (S)-1-chloroacetyl-2-cyano-pyrrolidine (690 mg, 4.0 mmol) and stirred at room temperature for 16 h. The mixture was combined with methylene chloride (50 mL), filtered through Celite®, the filter cake rinsed with methylene chloride, and the filtrate concentrated in vacuo (exhaustively to remove DMF). The crude residue was loaded onto a silica gel column (~125 cc) and eluted with 4:1 methylene chloride/methanol to afford (S,S)-1,4-bis[(2-(2-cyanopyrrolidin-1-yl)-2-oxo)ethylamino]bicyclo[2.2.2]-octane (160 mg, 10%) as a white solid, then eluted with 83:15:2 methylene chloride/methanol/ammonium hydroxide to afford (S)-(1-(1 aminobicyclo[2.2.2]oct-4-yl)aminoacetyl)-2-cyanopyrrolidine (715 mg, 65%) as a waxy white solid. Finally, the column was eluted with 70:23:7 methylene chloride/methanol/-ammonium hydroxide to afford recovered 1,4-diaminobicyclo[2.2.2]octane free base 373 mg).

(S,S)-1,4-bis[(2-(2-cyanopyrrolidin-1-yl)-2-oxo)ethylamino]bicyclo[2.2.2]octane: [M+H]$^+$=413.4. $^1$H NMR (CDCl$_3$) δ 4.70-4.90 (m, 2H), 3.25-3.75 (m, 8H), 2.00-2.40 (m, 8H), 1.60 (br s, 12H).

(S)-(1-(1-aminobicyclo[2.2.2]oct-4-yl)aminoacetyl)-2-cyanopyrrolidine: [M+H]$^+$=277.3. $^1$H NMR (d6-DMSO) δ 4.70 (m, 1H), 3.57 (m, 1H), 3.37 (m, 1H), 3.24 (m, 2H), 1.85-2.20 (m, 4H), 1.45 (br s, 12H).

EXAMPLE 33

(S)-(1-(1-Aminobicyclo[3.2.1]oct-3-yl)aminoacetyl)-2-cyanopyrrolidine

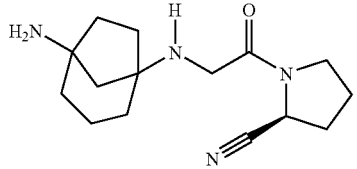

A solution of 1,3-diaminobicyclo[3.2.1]octane free base (743 mg, 5.3 mmol) and potassium carbonate (3.18 g, 23 mmol) in anhydrous N,N-dimethylformamide (DMF, 10 mL) under nitrogen was treated with (S)-1-chloroacetyl-2-cyano-pyrrolidine (483 mg, 2.8 mmol) and stirred at room temperature for 18 h. The mixture was combined with methylene chloride (35 mL), filtered through Celite®, the filter cake rinsed with methylene chloride, and the filtrate concentrated in vacuo (exhaustively to remove DMF). The crude residue was loaded onto a silica gel column (~100 cc) and eluted with 4:1 methylene chloride/methanol to afford (S,S)-1,3-bis[(2-(2-cyanopyrrolidin-1-yl)-2-oxo)ethylamino]bicyclo[3.2.1]-octane (204 mg, 18%) as a pale yellow foam, then eluted with 83:15:2 methylene chloride/methanol/ammonium hydroxide to afford (S)-(1-(1-aminobicyclo[3.2.1]oct-3-yl)aminoacetyl)-2-cyanopyrrolidine (568 mg, 73%) as a pale yellow oil. Finally, the column was eluted with 70:23:7 methylene chloride/methanol/-ammonium hydroxide to afford recovered 1,3-diaminobicyclo[3.2.1]octane free base (210 mg).

(S,S)-1,3-bis[(2-(2-cyanopyrrolidin-1-yl)-2-oxo)ethylamino]bicyclo[3.2.1]octane: [M+H]$^+$=413.3. $^1$H NMR (CDCl$_3$) δ 4.70-4.85 (m, 2H), 3.30-3.70 (m, 8H), 2.00-2.40 (m, 8H), 1.40-1.80 (m, 12H).

(S)-(1-(1-aminobicyclo[3.2.1]oct-3-yl)aminoacetyl)-2-cyanopyrrolidine: [M+H]$^+$=277.4. $^1$H NMR (CDCl$_3$) δ 4.70-4.85 (m, 1H), 3.30-3.70 (m, 4H), 2.00-2.40 (m, 4H), 1.40-1.80 (m, 12H).

EXAMPLE 34

(S)-1-[(3-(4-(trifluoromethyl)phenyl)sulfonamido-1-adamantyl)amino]acetyl-2-cyano-pyrrolidine

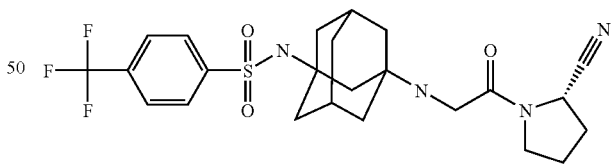

To a solution of (S)-1-[(3-amino-1-adamantyl)amino]acetyl-2-cyano-pyrrolidine (100 mg, 0.33 mmol) in 2 mL of tetrahydrofuran was added triethylamine (100 μl, 1 mmol). The 4-(trifluoromethyl)phenyl sulfonyl chloride was prepared in advance as a 0.33 M solution in dry THF. The sulfonyl chloride solution (1.0 mL, 0.33 mmol) was added drop wise to the stirring amine solution and the reaction ran at room temperature for 18 hours. The crude reaction mixture was evaporated to dryness, diluted to 1 mL in CH$_2$Cl$_2$ and loaded onto 5 g of silica gel. 3 column volumes of CH$_2$Cl$_2$ followed by 3 column volumes of 10% MeOH in CH$_2$Cl$_2$ used to elute the product (81 mg, 48.1% yield). MS (ESI) m/z=511 (M+H)$^+$.

EXAMPLE 35

2-(3-(2-((S)-2-cyanopyrrolidin-1-yl)-2-oxoethylamino)-adamantylamino)-4-bromo-pyrimidine

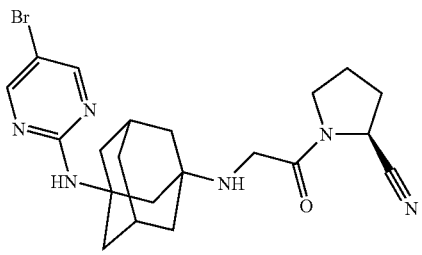

To 2-chloro-4-bromopyrimidine (253 mg, 1.32 mmol) was added (S)-1-[(3-amino-1-adamantyl)amino]acetyl-2-cyanopyrrolidine (100 mg, 0.33 mmol) in 0.25 mL of DMF. The reaction was heated to 90° C. and held at that temperature for 18 hrs. The crude reaction mixture was evaporated to dryness and diluted to 2 mL in 3/1 acetonitrile: water. The sample was purified by reverse phase HPLC with mass directed fractionation using an acetonitrile/water gradient with TFA as a modifier. After lyophilization, 1.0 mg of the mono-TFA salt was isolated. 0.5% yield. MS (ESI) m/z=459/461 (M+H)+.

EXAMPLES 36-62

Synthesis of Additional Active Compounds

The following compounds were made by procedures analogous to those described above, particularly the procedures described in Example 4, Example 10, Example 39, and Example 40 above.

| | Structure | Procedure of Example: | percent yield | MS (ESI) m/z |
|---|---|---|---|---|
| 36 | 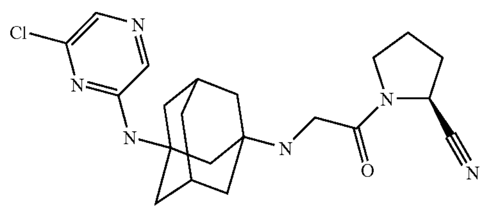 | 35 | 1.1 | 415 (M + H)+ |
| 37 | 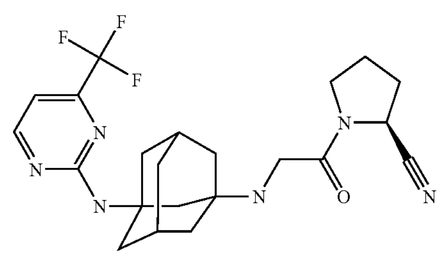 | 35 | 1.6 | 449 (M + H)+ |
| 38 | 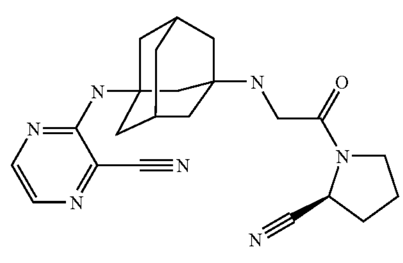 | 35 | 1.6 | 406 (M + H)+ |
| 39 | 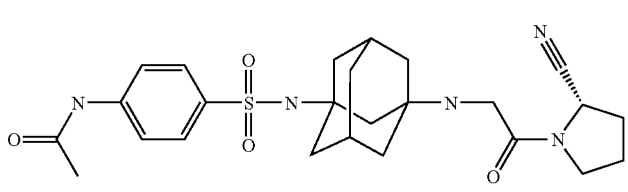 | 4 | 38.5 | 500 (M + H)+ |

-continued

| | Structure | Procedure of Example: | percent yield | MS (ESI) m/z |
|---|---|---|---|---|
| 40 | 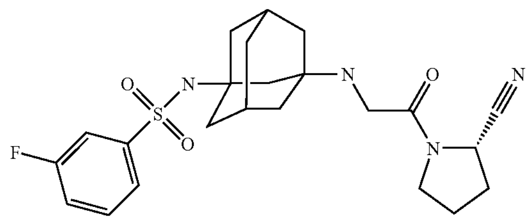 | 4 | 52.7 | 461 (M + H)+ |
| 41 | 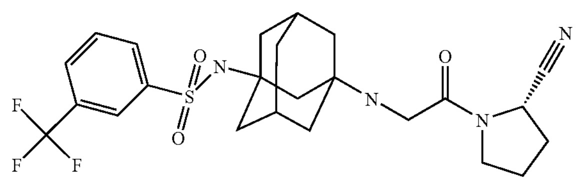 | 34 | 50.4 | 511 (M + H)+ |
| 42 | 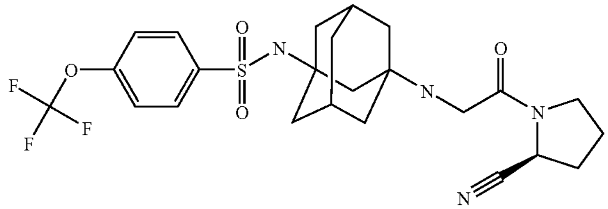 | 4 | 7.7 | 527 (M + H)+ |
| 43 | 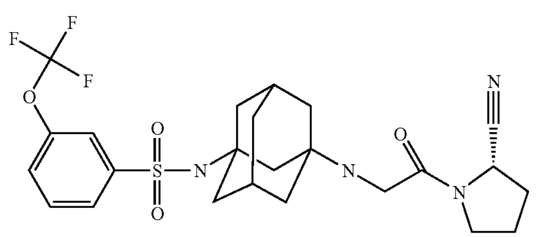 | 4 | 5.8 | 527 (M + H)+ |
| 44 | 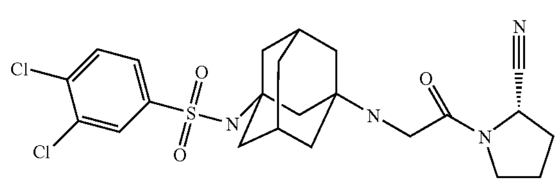 | 34 | 13.6 | 511/513 (M + H)+ |
| 45 | 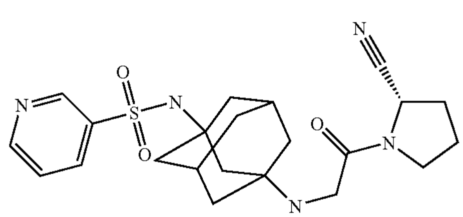 | 4 | 60.9 | 444 (M + H)+ |
| 46 | 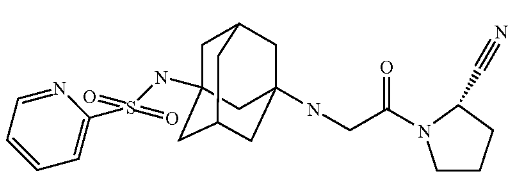 | 4 | 25.4 | 444 (M + H)+ |

-continued

| | Structure | Procedure of Example: | percent yield | MS (ESI) m/z |
|---|---|---|---|---|
| 47 | 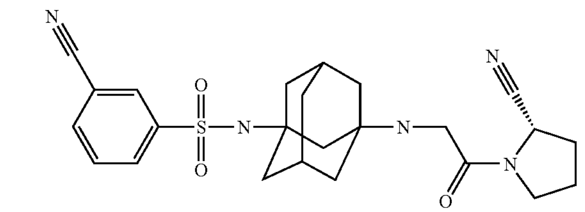 | 4 | 49.0 | 468 (M + H)+ |
| 48 | 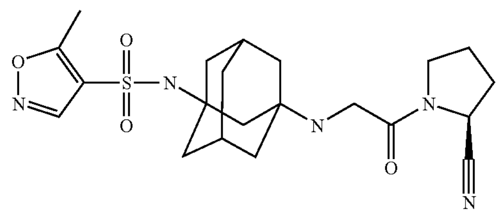 | 4 | 20.3 | 448 (M + H)+ |
| 49 | 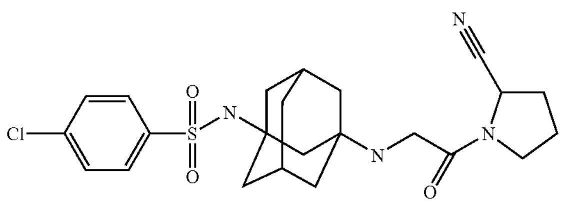 | 4 | 53.4 | 477 (M + H)+ |
| 50 | 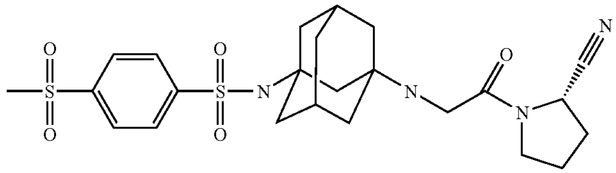 | 34 | 43.1 | 521 (M + H)+ |
| 51 | 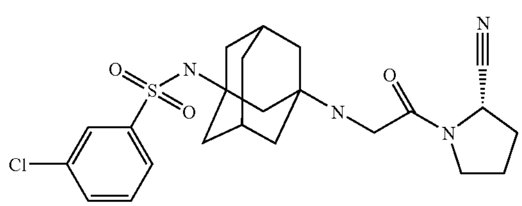 | 34 | 85.1 | 477 (M + H)+ |
| 52 | 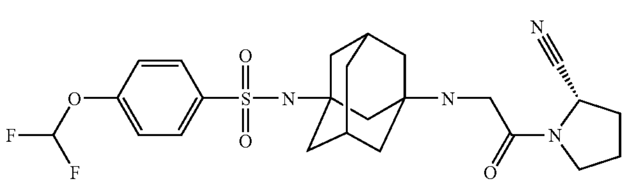 | 4 | 55.7 | 509 (M + H)+ |
| 53 | 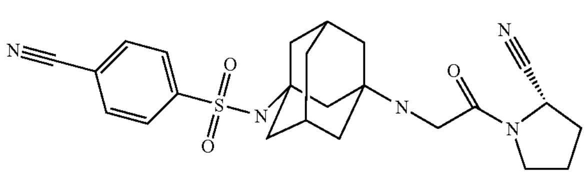 | 4 | 54.7 | 468 (M + H)+ |

-continued

| | Structure | Procedure of Example: | percent yield | MS (ESI) m/z |
|---|---|---|---|---|
| 54 | 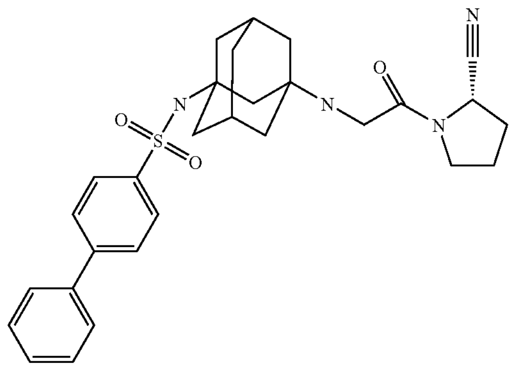 | 4 | 7.2 | 519 (M + H)+ |
| 55 | 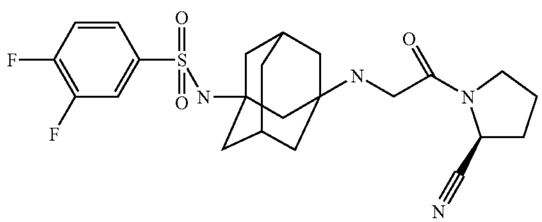 | 4 | 49.4 | 479 (M + H)+ |
| 56 | 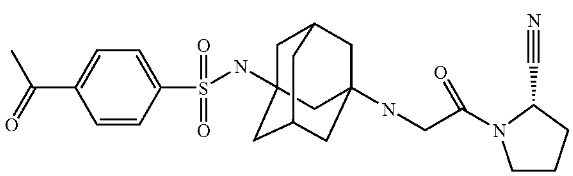 | 34 | 34.4 | 485 (M + H)+ |
| 57 | 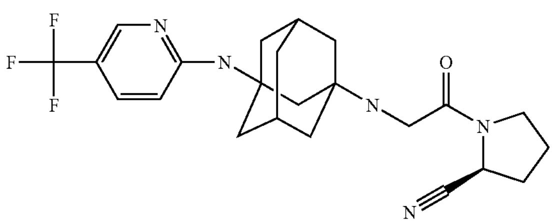 | 35 | 5.0 | 448 (M + H)+ |
| 58 | 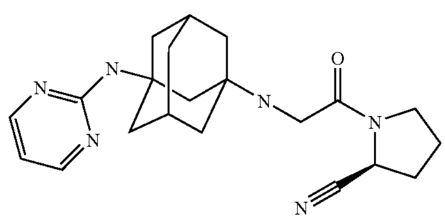 | 35 | 15.0 | 381 (M + H)+ |
| 59 | 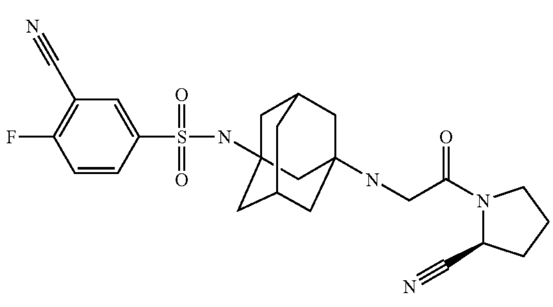 | 4 | 10.1 | 486 (M + H)+ |

-continued

| | Structure | Procedure of Example: | percent yield | MS (ESI) m/z |
|---|---|---|---|---|
| 60 | 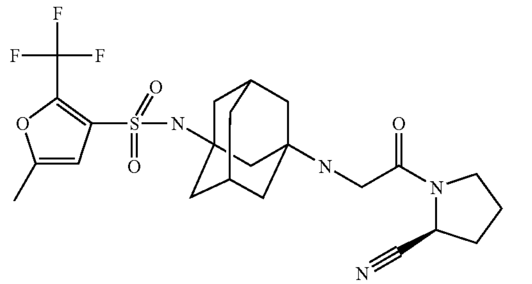 | 4 | 21.7 | 515 (M + H)+ |
| 61 | 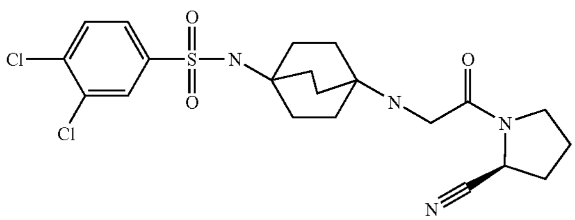 | 10 | 74.0 | 485/487 (M + H)+ |
| 62 | 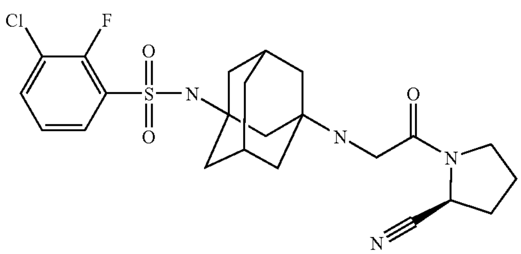 | 4 | 15.4 | 495 (M + H)+ |

EXAMPLE 63

Inhibition of dipeptidyl peptidase IV (DPP-IV) Activity

Porcine dipeptidyl peptidase IV (Sigma, D-7052) is used. Test compound and/or vehicle is pre-incubated with enzyme (70 μU/ml) in Tris-HCl pH 8.0 for 15 minutes at 37° C. Ala-Pro-AFC (20 μM) is then added for a further 30 minutes incubation period. The concentration of proteolytic product, AFC, is then read spectrofluorimetrically. 8 point concentration curves in duplicate are used to calculate $IC_{50}$ values, or percent inhibition is measured in duplicate at two dose levels.

TABLE 1

DPP-IV $IC_{50}$ values

| Compound number | $IC_{50}$ |
|---|---|
| (1) | 59 nM |
| (4) | 46 nM |
| (6) | 61 nM |
| (7) | 70 nM |

TABLE 2

Percent Inhibition of DPP-IV

| Compound number | Percent Inhibition at 1 uM | Percent Inhibition at 100 nM |
|---|---|---|
| (2) | 92 | 60 |
| (3) | 94 | 68 |
| (5) | 99 | 96 |

The foregoing is illustrative of the present invention, and is not to be construed as limiting thereof. The invention is defined by the following claims, with equivalents of the claims to be included therein.

That which is claimed is:

1. A compound of Formula I:

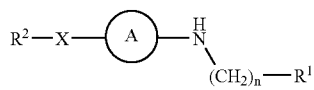

wherein:
X is $NR^3$;
n is 1 or 2;
A is adamantyl;

R¹ is

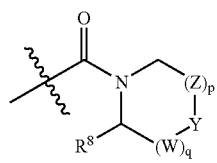

wherein:
p and q are independently 0 or 1, wherein p+q=1;
Y is CH₂, CHF, CF₂, O, or S(O)$_m$;
W and Z are independently CH₂, CHF, or CF₂;
and wherein the ring formed by N, W, Y, Z and the carbon atoms to which they are attached is saturated or optionally contains one double bond;
R² is R⁴—SO₂—; R⁵—SO₂—NH—C(O)—; or R⁶R⁷N—SO₂—;
R³ is selected from the group consisting of H, alkyl, haloalkyl, alkenyl, alkynyl, cycloalkyl, cycloalkylalkyl, aryl, arylalkyl, heterocyclo, and heterocycloalkyl;
R⁴ is selected from the group consisting of: haloalkyl, alkenyl, alkynyl, cycloalkyl, cycloalkylalkyl, aryl, arylalkyl, heterocyclo, and heterocycloalkyl;
R⁵ is selected from the group consisting of alkyl, haloalkyl, alkenyl, alkynyl, cycloalkyl, cycloalkylalkyl, aryl, arylalkyl, heterocyclo, and heterocycloalkyl;
R⁶ and R⁷ are each independently selected from the group consisting of: H, alkyl, haloalkyl, alkenyl, alkynyl, cycloalkyl, cycloalkylalkyl, aryl, arylalkyl, heterocyclo, and heterocycloalkyl; or R⁶ and R⁷ together form C3-C7 alkylene;
R⁸ is H or cyano;
m is 0, 1 or 2;
or a pharmaceutically acceptable salt thereof.

2. The compound of claim 1, wherein A is:

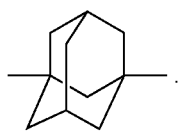

3. The compound of claim 1, wherein R² is R⁴—SO₂—.
4. The compound of claim 1, wherein R² is R⁵—SO₂—NH—C(O)—.
5. The compound of claim 1, wherein R² is R⁶R⁷N—SO₂—.
6. The compound of claim 1, wherein n is 1.
7. The compound of claim 1, wherein n is 2.
8. The compound of claim 1, wherein:
Y is selected from the group consisting of CHF, CF₂, O, and S(O)$_m$; or
q is 1 and W is selected from the group consisting of CHF and CF₂; or
p is 1 and Z is selected from the group consisting of CHF and CF₂.
9. The compound of claim 1, wherein:
Y is selected from the group consisting of CHF, CF₂, O, and S(O)$_m$;
q is 1 and W is CH₂; and
p is 0.

10. The compound of claim 1, wherein:
Y is selected from the group consisting of CHF, CF₂, O, and S(O)$_m$; or
q is 0; and
p is 1 and Z is CH₂.
11. The compound of claim 1, wherein:
Y is CH₂;
q is 1 and W is selected from the group consisting of CHF and CF₂; and
p is 0.
12. The compound of claim 1, wherein:
Y is CH₂;
q is 0; and
p is 1 and Z is selected from the group consisting of CHF and CF₂.
13. The compound of claim 1 selected from the group consisting of:

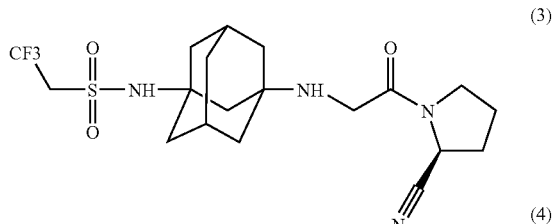
(3)

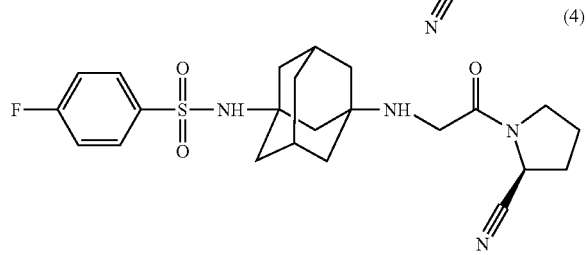
(4)

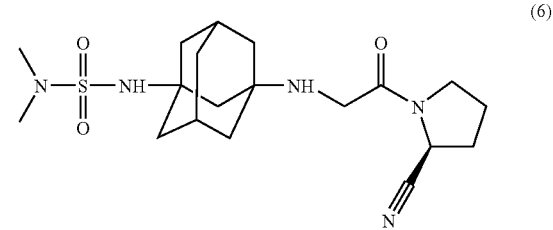
(6)

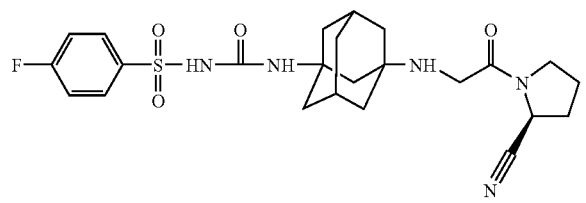
(7)

and pharmaceutically acceptable salts.

14. The compound according to claim 1 selected from the group consisting of:

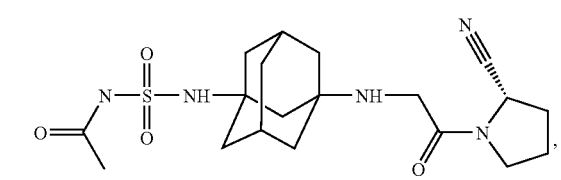

-continued
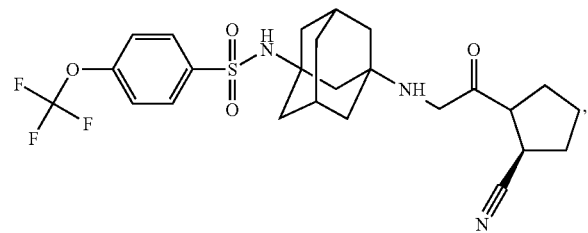
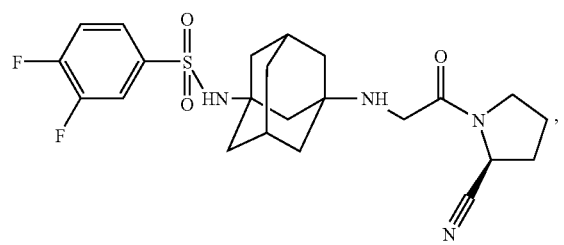
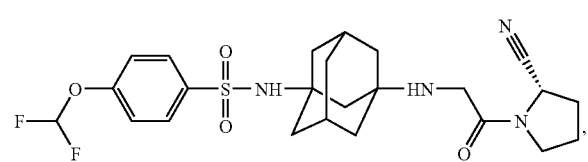
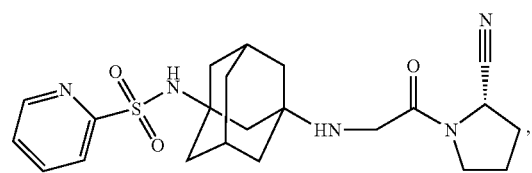
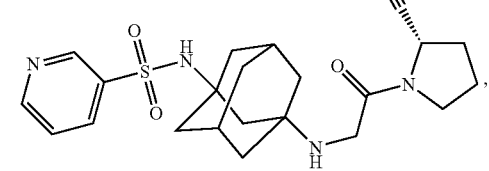
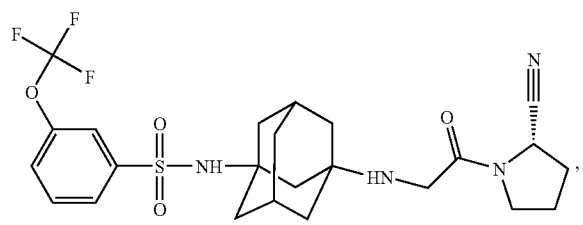
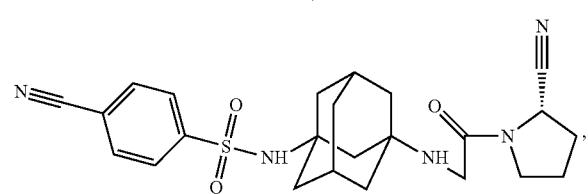
-continued
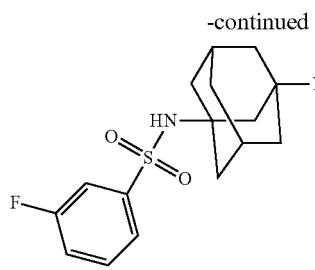
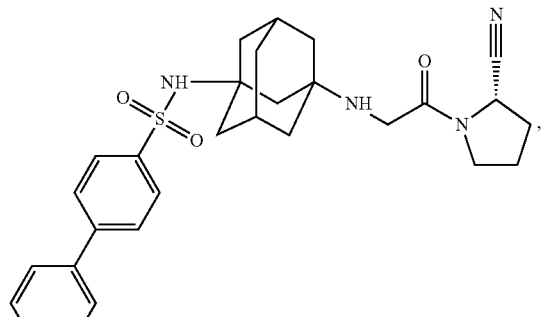
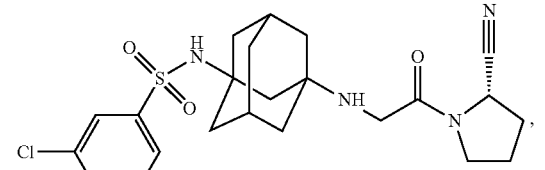
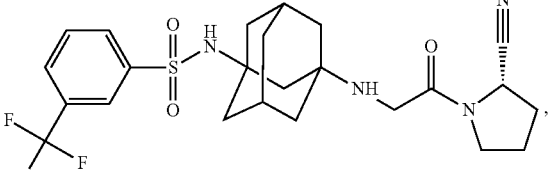
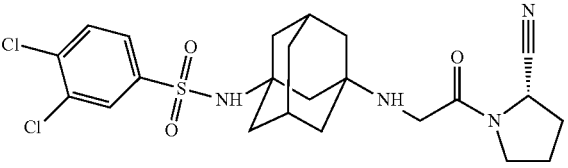
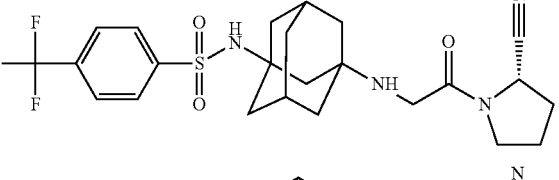
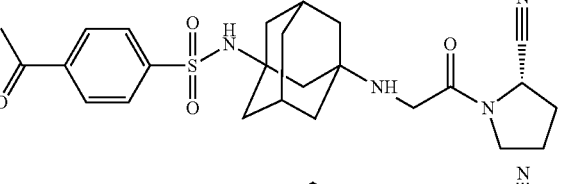
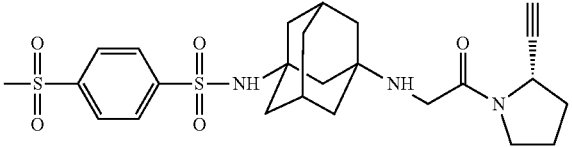

-continued
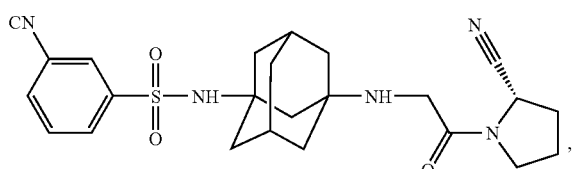
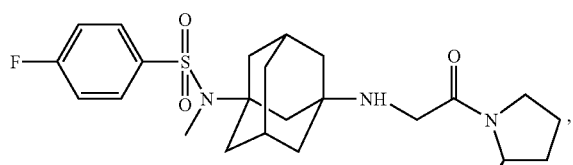
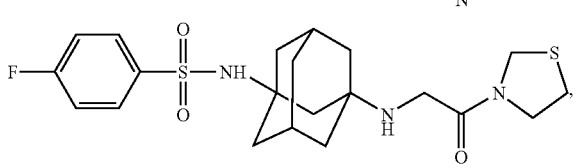
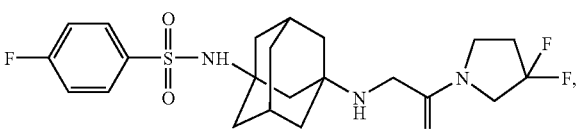
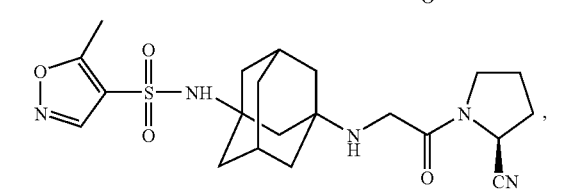
and pharmaceutically acceptable salts.
15. The compound of claim 1 selected from the group consisting of:
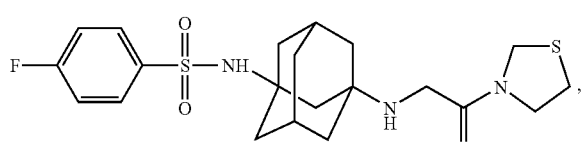
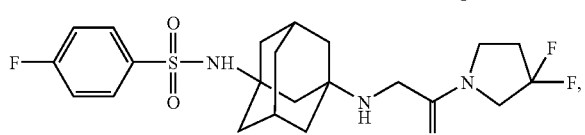
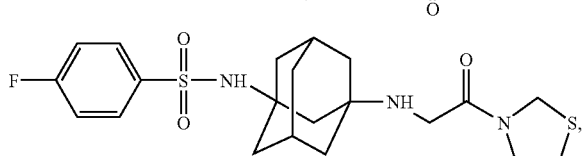
and pharmaceutically acceptable salts.
16. The compound of claim 1 selected from the group consisting of:
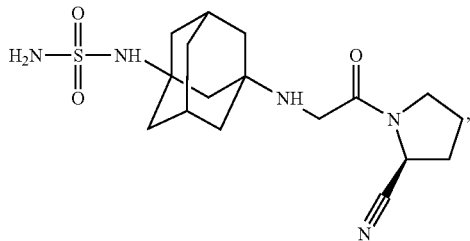
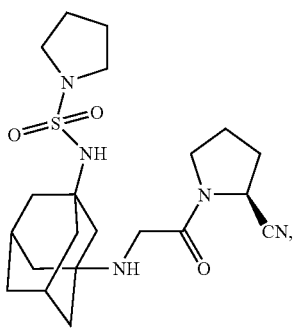
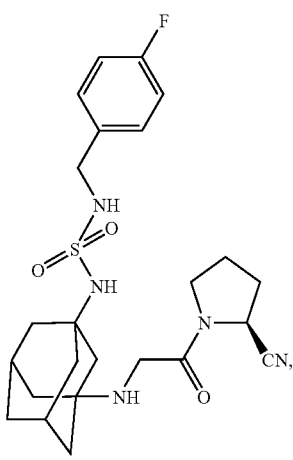
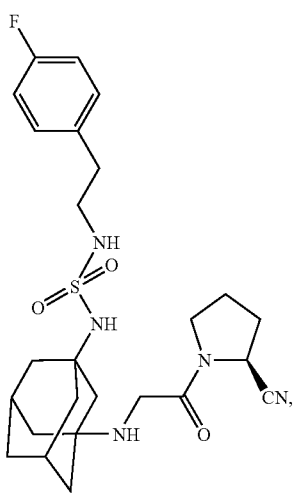
and pharmaceutically acceptable salts.

17. The compound of claim 1 selected from the group consisting of:

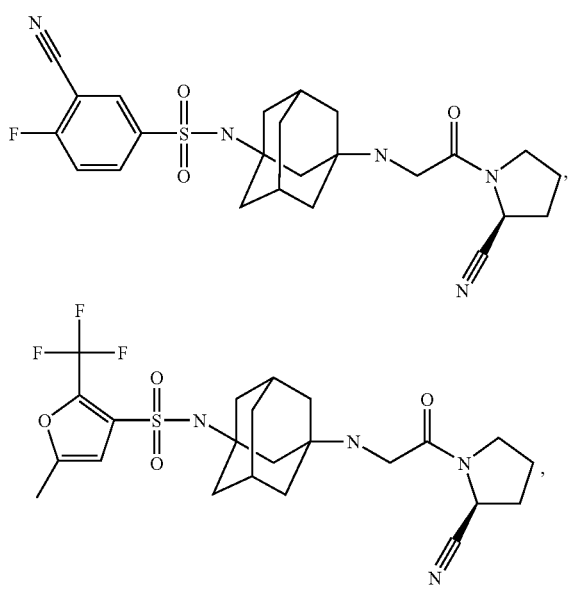

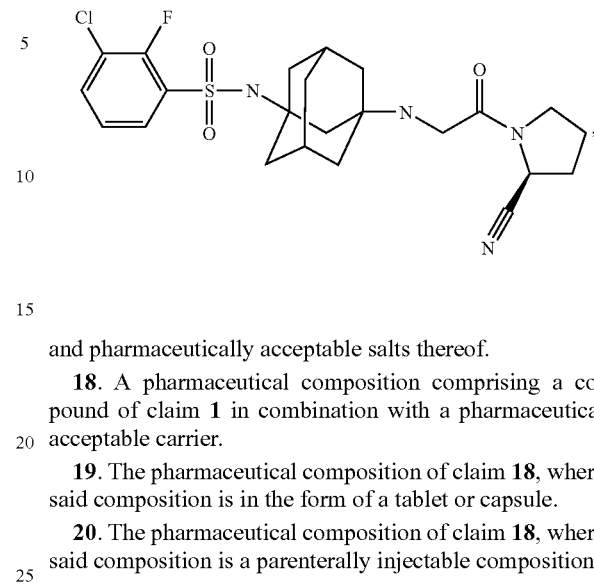

and pharmaceutically acceptable salts thereof.

18. A pharmaceutical composition comprising a compound of claim 1 in combination with a pharmaceutically acceptable carrier.

19. The pharmaceutical composition of claim 18, wherein said composition is in the form of a tablet or capsule.

20. The pharmaceutical composition of claim 18, wherein said composition is a parenterally injectable composition.

* * * * *

UNITED STATES PATENT AND TRADEMARK OFFICE
CERTIFICATE OF CORRECTION

PATENT NO.       : 7,842,707 B2
APPLICATION NO.  : 11/571857
DATED            : November 30, 2010
INVENTOR(S)      : Royalty et al.

It is certified that error appears in the above-identified patent and that said Letters Patent is hereby corrected as shown below:

In the Claims:
Column 50, Claim 13, Line 56: Please correct "acceptable salts."
           to read -- acceptable salts thereof. --

Column 51, Claim 14, Lines 4-10: Please correct

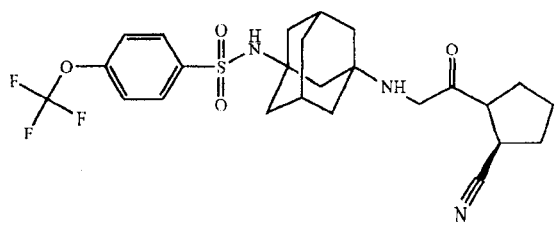

to read:

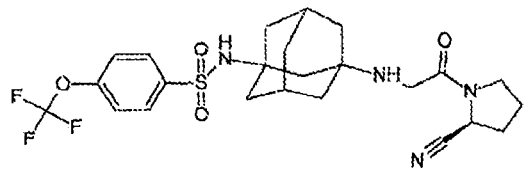

Column 53, Claim 14, Line 40: Please correct "acceptable salts."
          to read -- acceptable salts thereof. --
    Claim 15, Line 67: Please correct "acceptable salts."
          to read -- acceptable salts thereof. --

Column 54, Claim 16, Line 67: Please correct "acceptable salts."
          to read -- acceptable salts thereof. --

Signed and Sealed this
Twenty-eighth Day of June, 2011

David J. Kappos
*Director of the United States Patent and Trademark Office*